United States Patent
Juhasz et al.

(10) Patent No.: US 9,532,708 B2
(45) Date of Patent: Jan. 3, 2017

(54) ELECTRONICALLY CONTROLLED FIXATION LIGHT FOR OPHTHALMIC IMAGING SYSTEMS

(75) Inventors: Tibor Juhasz, Corona del Mar, CA (US); Guy Holland, San Clemente, CA (US); Ferenc Raksi, Mission Viejo, CA (US)

(73) Assignee: ALCON LENSX, INC., Aliso Viejo, CA (US)

(*) Notice: Subject to any disclaimer, the term of this patent is extended or adjusted under 35 U.S.C. 154(b) by 69 days.

(21) Appl. No.: 12/885,193

(22) Filed: Sep. 17, 2010

(65) Prior Publication Data

US 2012/0069302 A1 Mar. 22, 2012

(51) Int. Cl.
- *A61B 3/00* (2006.01)
- *A61B 3/10* (2006.01)
- *A61F 9/008* (2006.01)

(52) U.S. Cl.
CPC .......... *A61B 3/0091* (2013.01); *A61B 3/0075* (2013.01); *A61B 3/102* (2013.01); *A61F 9/008* (2013.01)

(58) Field of Classification Search
CPC ... A61B 3/0091; A61B 3/0008; A61B 3/0083; A61B 3/0075
USPC .................................................. 351/211, 221
See application file for complete search history.

(56) References Cited

U.S. PATENT DOCUMENTS

| | | |
|---|---|---|
| 4,164,222 A | 8/1979 | Prokhorov et al. |
| 4,198,143 A | 4/1980 | Karasawa |
| 4,235,529 A | 11/1980 | Kawase et al. |
| 4,465,348 A | 8/1984 | Lang |
| 4,520,816 A | 6/1985 | Schachar et al. |
| 4,533,222 A * | 8/1985 | Ishikawa ........................ 351/206 |
| 4,538,608 A | 9/1985 | L'Esperance, Jr. |
| 4,554,917 A | 11/1985 | Tagnon |

(Continued)

FOREIGN PATENT DOCUMENTS

| | | |
|---|---|---|
| EP | 1444946 | 8/2004 |
| EP | 1803390 | 7/2007 |

(Continued)

OTHER PUBLICATIONS

Carl Zeiss Meditec, Inc. Cirrus HD-OCT User Manual. Dublin, CA, USA: Carl Zeiss Meditec, 2009. Print.*

(Continued)

*Primary Examiner* — Zachary Wilkes
(74) *Attorney, Agent, or Firm* — S. Brannon Latimer

(57) ABSTRACT

An electronically controlled fixation light system is described for ophthalmic systems. The ophthalmic system can include an ophthalmic imaging device that generates an image of a portion of an imaged eye, a fixation light controller that includes an input module, configured to receive an input in relation to the image generated by the ophthalmic imaging device, and a control signal generator that generates an electronic fixation light control signal in response to the received input, and a fixation light source, configured to receive the fixation light control signal, and to generate a fixation light according to the received fixation light control signal. A surgeon can image a portion of an eye with the imaging device, determine a misalignment of the imaged eye relative to the imaging device based on the image, and control the fixation light with an electronic control signal to reduce the determined misalignment.

20 Claims, 15 Drawing Sheets

(56) References Cited

U.S. PATENT DOCUMENTS

| | | |
|---|---|---|
| 4,638,801 A | 1/1987 | Daly et al. |
| 4,764,005 A | 8/1988 | Webb et al. |
| 4,881,808 A | 11/1989 | Bille et al. |
| 4,901,718 A | 2/1990 | Bille et al. |
| 4,907,586 A | 3/1990 | Bille et al. |
| 5,048,946 A | 9/1991 | Sklar et al. |
| 5,049,147 A | 9/1991 | Danon |
| 5,054,907 A | 10/1991 | Sklar et al. |
| 5,098,426 A | 3/1992 | Sklar et al. |
| 5,112,328 A | 5/1992 | Taboada et al. |
| 5,139,022 A | 8/1992 | Lempert |
| 5,246,435 A | 9/1993 | Bille et al. |
| 5,255,025 A | 10/1993 | Volk |
| 5,286,964 A | 2/1994 | Fountain |
| 5,321,501 A | 6/1994 | Swanson et al. |
| 5,336,215 A | 8/1994 | Hsueh et al. |
| 5,391,165 A | 2/1995 | Fountain et al. |
| 5,439,462 A | 8/1995 | Bille et al. |
| 5,493,109 A | 2/1996 | Wei et al. |
| 5,512,965 A * | 4/1996 | Snook ............ 351/205 |
| 5,549,632 A | 8/1996 | Lai |
| 5,656,186 A | 8/1997 | Mourou et al. |
| 5,738,676 A | 4/1998 | Hammer et al. |
| 5,779,696 A | 7/1998 | Berry et al. |
| 5,795,295 A | 8/1998 | Hellmuth et al. |
| 5,936,706 A | 8/1999 | Takagi |
| 5,954,648 A | 9/1999 | Van Der Brug |
| 5,954,711 A | 9/1999 | Ozaki et al. |
| 5,994,690 A | 11/1999 | Kulkarni et al. |
| 6,004,314 A | 12/1999 | Wei et al. |
| 6,045,227 A * | 4/2000 | Stewart et al. ............ 351/237 |
| 6,095,648 A | 8/2000 | Birngruber et al. |
| 6,099,522 A | 8/2000 | Knopp et al. |
| 6,137,585 A | 10/2000 | Hitzenberger et al. |
| 6,254,595 B1 | 7/2001 | Juhasz et al. |
| 6,288,784 B1 | 9/2001 | Hitzenberger et al. |
| 6,314,311 B1 | 11/2001 | Williams et al. |
| 6,317,616 B1 | 11/2001 | Glossop |
| 6,337,925 B1 | 1/2002 | Cohen et al. |
| 6,377,349 B1 | 4/2002 | Fercher |
| 6,379,005 B1 | 4/2002 | Williams et al. |
| 6,451,009 B1 | 9/2002 | Dasilva et al. |
| 6,454,761 B1 | 9/2002 | Freedman |
| 6,497,701 B2 | 12/2002 | Shimmick et al. |
| 6,529,758 B2 | 3/2003 | Shahidi |
| 6,579,282 B2 | 6/2003 | Bille et al. |
| 6,623,476 B2 | 9/2003 | Juhasz et al. |
| 6,636,696 B2 * | 10/2003 | Saito ............ 351/208 |
| 6,687,010 B1 | 2/2004 | Horii et al. |
| 6,730,074 B2 | 5/2004 | Bille et al. |
| 6,741,359 B2 | 5/2004 | Wei et al. |
| 6,751,033 B2 | 6/2004 | Goldstein et al. |
| 6,755,819 B1 | 6/2004 | Waelti |
| 6,763,259 B1 | 7/2004 | Hauger et al. |
| 6,769,769 B2 | 8/2004 | Podoleanu et al. |
| 6,775,007 B2 | 8/2004 | Izatt et al. |
| 6,863,667 B2 | 3/2005 | Webb et al. |
| 6,887,232 B2 | 5/2005 | Bille |
| 6,899,707 B2 | 5/2005 | Scholler et al. |
| 6,932,807 B1 | 8/2005 | Tomita et al. |
| 6,991,629 B1 | 1/2006 | Juhasz et al. |
| 6,996,905 B2 | 2/2006 | Meguro |
| 7,006,232 B2 | 2/2006 | Rollins et al. |
| 7,018,376 B2 | 3/2006 | Webb et al. |
| 7,027,233 B2 | 4/2006 | Goldstein et al. |
| 7,044,602 B2 * | 5/2006 | Chernyak ............ 351/208 |
| 7,061,622 B2 | 6/2006 | Rollins et al. |
| 7,072,047 B2 | 7/2006 | Westphal et al. |
| 7,079,254 B2 | 7/2006 | Kane et al. |
| 7,102,756 B2 | 9/2006 | Izatt et al. |
| 7,113,818 B2 | 9/2006 | Podoleanu et al. |
| 7,126,693 B2 | 10/2006 | Everett et al. |
| 7,130,054 B2 | 10/2006 | Ostrovsky et al. |
| 7,133,137 B2 | 11/2006 | Shimmick |
| 7,139,077 B2 | 11/2006 | Podoleanu et al. |
| 7,145,661 B2 | 12/2006 | Hitzenberger |
| 7,148,970 B2 | 12/2006 | de Boer |
| 7,184,148 B2 | 2/2007 | Alphonse |
| 7,207,983 B2 | 4/2007 | Hahn et al. |
| 7,248,371 B2 | 7/2007 | Chan et al. |
| 7,268,885 B2 | 9/2007 | Chan et al. |
| 7,280,221 B2 | 10/2007 | Wei |
| 7,307,733 B2 | 12/2007 | Chan et al. |
| 7,310,150 B2 | 12/2007 | Guillermo et al. |
| 7,312,876 B2 | 12/2007 | Chan et al. |
| 7,319,566 B2 | 1/2008 | Prince et al. |
| 7,329,002 B2 * | 2/2008 | Nakanishi ............ 351/200 |
| 7,330,270 B2 | 2/2008 | O'Hara et al. |
| 7,330,273 B2 | 2/2008 | Podoleanu et al. |
| 7,335,223 B2 | 2/2008 | Obrebski |
| 7,336,366 B2 | 2/2008 | Choma et al. |
| 7,342,659 B2 | 3/2008 | Horn et al. |
| 7,347,548 B2 | 3/2008 | Huang et al. |
| 7,352,444 B1 | 4/2008 | Seams et al. |
| 7,355,716 B2 | 4/2008 | de Boer et al. |
| 7,364,296 B2 | 4/2008 | Miller et al. |
| 7,365,856 B2 | 4/2008 | Everett et al. |
| 7,365,859 B2 | 4/2008 | Yun et al. |
| 7,370,966 B2 | 5/2008 | Fukuma et al. |
| 7,371,230 B2 | 5/2008 | Webb et al. |
| 7,372,578 B2 | 5/2008 | Akiba et al. |
| 7,377,642 B2 * | 5/2008 | Ishihara et al. ............ 351/206 |
| 7,388,672 B2 | 6/2008 | Zhou et al. |
| 7,390,089 B2 | 6/2008 | Loesel et al. |
| 7,400,410 B2 | 7/2008 | Baker et al. |
| 7,402,159 B2 | 7/2008 | Loesel et al. |
| 7,426,037 B2 | 9/2008 | Ostrovsky et al. |
| 7,433,046 B2 | 10/2008 | Everett et al. |
| 7,452,077 B2 | 11/2008 | Meyer et al. |
| 7,452,080 B2 * | 11/2008 | Wiltberger et al. ............ 351/211 |
| 7,461,658 B2 | 12/2008 | Jones et al. |
| 7,466,423 B2 | 12/2008 | Podoleanu et al. |
| 7,470,025 B2 * | 12/2008 | Iwanaga ............ 351/211 |
| 7,477,764 B2 | 1/2009 | Haisch |
| 7,480,058 B2 | 1/2009 | Zhao et al. |
| 7,480,059 B2 | 1/2009 | Zhou et al. |
| 7,488,070 B2 | 2/2009 | Hauger et al. |
| 7,488,930 B2 | 2/2009 | Ajgaonkar et al. |
| 7,492,466 B2 | 2/2009 | Chan et al. |
| 7,503,916 B2 | 3/2009 | Shimmick |
| 7,508,525 B2 | 3/2009 | Zhou et al. |
| 7,535,577 B2 | 5/2009 | Podoleanu et al. |
| 7,537,591 B2 | 5/2009 | Feige et al. |
| 7,557,928 B2 | 7/2009 | Ueno |
| 7,575,322 B2 | 8/2009 | Somani |
| 7,593,559 B2 | 9/2009 | Toth et al. |
| 7,602,500 B2 | 10/2009 | Izatt et al. |
| 7,604,351 B2 | 10/2009 | Fukuma et al. |
| 7,614,744 B2 | 11/2009 | Abe |
| 7,630,083 B2 | 12/2009 | de Boer et al. |
| 7,631,970 B2 | 12/2009 | Wei |
| 7,633,627 B2 | 12/2009 | Choma et al. |
| 7,643,152 B2 | 1/2010 | de Boer et al. |
| 7,797,119 B2 | 9/2010 | De Boer et al. |
| 7,813,644 B2 | 10/2010 | Chen et al. |
| 7,898,712 B2 | 3/2011 | Adams et al. |
| 8,223,143 B2 * | 7/2012 | Dastmalchi et al. ............ 345/418 |
| 8,394,084 B2 | 3/2013 | Palankar et al. |
| 2001/0022648 A1 | 9/2001 | Lai |
| 2002/0013574 A1 | 1/2002 | Elbrecht et al. |
| 2002/0082466 A1 | 6/2002 | Han |
| 2002/0097374 A1 | 7/2002 | Payne et al. |
| 2002/0133145 A1 | 9/2002 | Gerlach et al. |
| 2002/0198516 A1 | 12/2002 | Knopp |
| 2003/0090674 A1 | 5/2003 | Zeylikovich et al. |
| 2003/0206272 A1 | 11/2003 | Cornsweet et al. |
| 2004/0039378 A1 | 2/2004 | Lin |
| 2004/0059321 A1 | 3/2004 | Knopp et al. |
| 2004/0151466 A1 | 8/2004 | Crossman-Bosworth et al. |
| 2004/0243233 A1 | 12/2004 | Phillips |
| 2005/0010109 A1 | 1/2005 | Faul |
| 2005/0015120 A1 | 1/2005 | Seibel et al. |
| 2005/0021011 A1 | 1/2005 | LaHaye |
| 2005/0173817 A1 | 8/2005 | Fauver et al. |

(56) References Cited

U.S. PATENT DOCUMENTS

| | | |
|---|---|---|
| 2005/0192562 A1 | 9/2005 | Loesel et al. |
| 2005/0201633 A1 | 9/2005 | Moon et al. |
| 2005/0203492 A1 | 9/2005 | Nguyen et al. |
| 2005/0215986 A1 | 9/2005 | Chernyak et al. |
| 2005/0284774 A1 | 12/2005 | Mordaunt |
| 2005/0286019 A1 | 12/2005 | Wiltberger et al. |
| 2005/0288745 A1 | 12/2005 | Andersen et al. |
| 2006/0020172 A1 | 1/2006 | Luerssen et al. |
| 2006/0077346 A1 | 4/2006 | Matsumoto |
| 2006/0100613 A1 | 5/2006 | McArdle et al. |
| 2006/0179992 A1 | 8/2006 | Kermani |
| 2006/0187462 A1 | 8/2006 | Srinivasan et al. |
| 2006/0195076 A1 | 8/2006 | Blumenkranz et al. |
| 2006/0206102 A1 | 9/2006 | Shimmick |
| 2007/0013867 A1 | 1/2007 | Ichikawa |
| 2007/0121069 A1 | 5/2007 | Andersen et al. |
| 2007/0126985 A1 | 6/2007 | Wiltberger et al. |
| 2007/0129709 A1 | 6/2007 | Andersen et al. |
| 2007/0129775 A1 | 6/2007 | Mordaunt et al. |
| 2007/0147730 A1 | 6/2007 | Wiltberger et al. |
| 2007/0173791 A1 | 7/2007 | Raksi |
| 2007/0173794 A1 | 7/2007 | Frey et al. |
| 2007/0173795 A1 | 7/2007 | Frey et al. |
| 2007/0185475 A1 | 8/2007 | Frey et al. |
| 2007/0189664 A1 | 8/2007 | Andersen et al. |
| 2007/0216909 A1 | 9/2007 | Everett et al. |
| 2007/0219541 A1 | 9/2007 | Kurtz |
| 2007/0230520 A1 | 10/2007 | Mordaunt et al. |
| 2007/0282313 A1 | 12/2007 | Huang et al. |
| 2007/0291277 A1* | 12/2007 | Everett et al. ............ 356/497 |
| 2007/0299429 A1 | 12/2007 | Amano |
| 2008/0033406 A1 | 2/2008 | Andersen et al. |
| 2008/0049188 A1 | 2/2008 | Wiltberger et al. |
| 2008/0055543 A1 | 3/2008 | Meyer et al. |
| 2008/0056610 A1 | 3/2008 | Kanda |
| 2008/0071254 A1 | 3/2008 | Lummis et al. |
| 2008/0088795 A1 | 4/2008 | Goldstein et al. |
| 2008/0100612 A1 | 5/2008 | Dastmalchi et al. |
| 2008/0281303 A1 | 11/2008 | Culbertson et al. |
| 2008/0281413 A1 | 11/2008 | Culbertson et al. |
| 2008/0319427 A1 | 12/2008 | Palanker |
| 2009/0012507 A1 | 1/2009 | Culbertson et al. |
| 2009/0088734 A1 | 4/2009 | Mordaunt |
| 2009/0125005 A1 | 5/2009 | Chernyak et al. |
| 2009/0131921 A1 | 5/2009 | Kurtz et al. |
| 2009/0149742 A1 | 6/2009 | Kato et al. |
| 2009/0157062 A1 | 6/2009 | Hauger et al. |
| 2009/0161827 A1 | 6/2009 | Gertner et al. |
| 2009/0163898 A1* | 6/2009 | Gertner et al. ............ 351/246 |
| 2009/0168017 A1 | 7/2009 | O'Hara et al. |
| 2009/0268161 A1 | 10/2009 | Hart et al. |
| 2010/0004641 A1 | 1/2010 | Frey et al. |
| 2010/0004643 A1 | 1/2010 | Frey et al. |
| 2010/0007848 A1 | 1/2010 | Murata |
| 2010/0022994 A1 | 1/2010 | Frey et al. |
| 2010/0022995 A1 | 1/2010 | Frey et al. |
| 2010/0022996 A1 | 1/2010 | Frey et al. |
| 2010/0042079 A1 | 2/2010 | Frey et al. |
| 2010/0110377 A1 | 5/2010 | Maloca et al. |
| 2010/0324543 A1 | 12/2010 | Kurtz et al. |
| 2011/0022036 A1 | 1/2011 | Frey et al. |
| 2011/0118609 A1 | 5/2011 | Goldshleger et al. |
| 2011/0304819 A1 | 12/2011 | Juhasz et al. |
| 2011/0319873 A1 | 12/2011 | Raksi et al. |
| 2012/0274903 A1 | 11/2012 | Sayeram et al. |

FOREIGN PATENT DOCUMENTS

| | | |
|---|---|---|
| EP | 1972266 | 9/2008 |
| JP | 2002345758 | 12/2002 |
| JP | 2009-112431 | 5/2009 |
| WO | 98/08048 | 2/1998 |
| WO | 03/062802 | 7/2003 |
| WO | 2006074469 | 7/2006 |
| WO | WO2007106326 | 9/2007 |
| WO | 2007/130411 | 11/2007 |

OTHER PUBLICATIONS

Nidek Co. Ltd. Model Tonoref II Operator's Manual. Tokyo, Japan: Nidek, 2007. Print.*

Kim, Tae Hoon, Authorized Officer, Korean Intellectual Property Office, PCT International Application No. PCT/US2011/025332, in International Search Report, mailed Sep. 16, 2011, 8 pages.

PCT International Search Report and Written Opinion dated Feb. 9, 2012 for International Application Serial No. PCT/US2011/040223.

Kamensky et al.; "In situ monitoring of the middle IR laser ablation of a cataract-suffered human lens by optical coherent tomography"; Proc. SPIE; 2930: 222-229 (1996).

Kamensky et al.; "Monitoring and animation of laser ablation process in cataracted eye lens using coherence IDS 41 tomography"; Proc. SPIE; 2981: 94-102 (1997).

PCT International Search Report for International Application Serial No. PCT/US2011/023710 mailed Aug. 24, 2011.

PCT International Search Report for International Application Serial No. PCT/US2010/056701 mailed Aug. 24, 2011.

Swanson et al.; "In vivo retinal imaging by optical coherence tomography"; Optics Letters; vol. 18; No. 21; pp. 1864-1866 (Nov. 1993).

RE 90/006,816, filed Feb. 27, 2007, Swanson et al.

Arimoto et al., "Imaging Properties of Axicon in a Scanning Optical System," Nov. 1, 1992, Applied Optics, 31(31): 6652-6657, 5 pages.

Birngruber et al., "In-Vivo Imaging of the Development of Linear and Non-Linear Retinal Laser Effects Using Optical Coherence Tomography in Correlation with Histopathological Findings," 1995, Proc. SPIE 2391:21-27, 7 pages.

Chinn, S.R., et al., "Optical coherence tomography using a frequency-tunable optical source," *Optics Letters*, 22(5):340-342, Mar. 1997.

Fercher et al., "Eye-Length Measurement by Interferometry With Partially Coherent Light," Mar. 1988, Optics Letters, 13(3):186-188, 3 pages.

Fercher et al., "Measurement of Intraocular Distances by Backscattering Spectral Interferometry," May 15, 1995, Optics Comm. 117:43-48, 6 pages.

Huber, R., et al., "Three-dimensional and C-mode OCT imaging with a compact, frequency swept laser source at 1300 nm," *Optics Express*, 13(26):10523-10538, Dec. 2005.

International Search Report and Written Opinion dated Mar. 12, 2009 for International Application No. PCT/US2008/075511, filed Sep. 5, 2008 (9 pages).

Izatt et al., Micron-Resolution Biomedical Imaging With Optical Coherence Tomography, Oct. 1993, Optics & Photonics News, pp. 14-19, 6 pages.

Massow, O., et al., "Femtosecond laser microsurgery system controlled by optical coherence tomography," *Proceedings of the SPIE—Commercial and Biomedical Applications of Ultrafast Lasers VIII*, vol. 6881, pp. 688106(1)-688106(6), Mar. 2008, 6 pages.

Massow, O., et al., "Optical coherence tomography controlled femtosecond laser microsurgery system," *Proceedings of the SPIE—Optical Coherence Tomography and Coherence Techniques III*, vol. 6627, pp. 662717(1)-662717(6), Aug. 2007.

Ohmi, M., et al., "In-situ Observation of Tissue Laser Ablation Using Optical Coherence Tomography," *Optical and Quantum Electronics*, 37(13-15):1175-1183, Dec. 2005, 9 pages.

Sarunic, M., et al., "Imaging the Ocular Anterior Segment With Real-Time, Full-Range Fourier-Domain Optical Coherence Tomography," *Archives of Ophthalmology*, 126(4):537-542, Apr. 2008, 6 pages.

Sarunic, M., et al., "Instantaneous complex conjugate resolved spectral domain and swept-source OCT using 3x3 fiber couplers," *Optics Express*, 13(3):957-967, Feb. 2005 11 pages.

(56) References Cited

OTHER PUBLICATIONS

Stern et al., "Femtosecond Optical Ranging of Corneal Incision Depth," Jan. 1989, Investigative Ophthalmology & Visual Science, 30(1):99-104, 6 pages.

Swanson, et al., "Method and Apparatus for Optical Imaging with Means for Controlling the Longitudinal Range of the Sample," U.S. Re-exam Patent Application No. 90/006,816, filed Oct. 20, 2003.

Tao, Y., et al., "High-speed complex conjugate resolved retinal spectral domain optical coherence tomography using sinusoidal phase modulation," *Optics Letters*, 32(20):2918-2920, Oct. 2007, 3 pages.

Eurepean Patent Office, European Patent Application No. 10191057.8, in European Search Report, mailed Mar. 16, 2011, 3 pages.

Wojtkowski et al., "In Vivo Human Retinal Imaging by Fourier Domain Optical Coherence Tomography," Jul. 2002, Journal of Biomedical Optics 7(3):457-463, 7 pages.

Yun, S.H., et al., "Wavelength-swept fiber laser with frequency shifted feedback and resonantly swept intra-cavity acoustooptic tunable filter," *IEEE Journal of Selected Topics in Quantum Electronics*, 3(4):1087-1096, Aug. 1997.

Korean Intellectual Property Office, PCT International Application No. PCT/US2011/023710, in International Search Report, mailed Aug. 24, 2011, 8 pages.

Hee, M., et al., "Femotosecond Transillumination Optical Coherence Tomography," Optics Letters, Jun. 1993, pp. 950-952, 18(12).

PCT International Search Report and Written Opinion dated Apr. 10, 2012 for International Application No. PCT/US2011/051466 filed Sep. 13, 2011.

Ostaszewski et al., "Risley prism Beam Pointer", Proc. of SPIE, vol. 6304, 630406-1 thru 630406-10, 2006 [10 pages].

Sarunic, M., et al., "Real-time quadrature projection complex conjugate resolved Fourier domain optical coherence tomography", Optics Letters, 31(16):2426-2428, Aug. 2006.

Bagayev et al., "Optical coherence tomography for in situ monitoring of laser corneal ablation", Journal of Biomedical Optics, 7(4), pp. 633-642 (Oct. 2002).

Blaha et al., "The slit lamp and the laser in ophthalmology—a new laser slit lamp", SPIE Optical Instrumentation for Biomedical Laser Applications, vol. 658, pp. 38-42, 1986.

Boppart, S., et al., "Intraoperative Assessment of Microsurgery with Three-dimensional Optical Coherence Tomography", Radiology, 208(1):81-86, Jul. 1998.

Davidson, "Analytic Waveguide Solutions and the Coherence Probe Microscope", Microelectronic Engineering, 13, pp. 523-526, 1991.

Drexler, W., et al., "Measurement of the thickness of fundus layers by partial coherence tomography", Optical Engineering, 34(3):701-710, Mar. 1995.

Dyer, P., et al., "Optical Fibre Delivery and Tissue Ablation Studies using a Pulsed Hydrogen Fluoride Laser", Lasers in Medical Science, 7:331-340, 1992.

Fercher et al., "In Vivo Optical Coherence Tomography", American Journal of Ophthalmology, 116(1), pp. 113-114, 1993.

Fujimoto, J., et al., :Biomedical Imaging using Optical Coherent Tomography, 1994, 67.

Hammer, D., "Ultrashort pulse laser induced bubble creation thresholds in ocular media", SPIE, 2391:30-40, 1995.

Hauger, C., et al., "High speed low coherence interferometer for optical coherence tomography", Proceedings of SPIE, 4619:1-9, 2002.

Hee, M., et al., "Optical Coherence tomography of the Human Retina", Arch Ophthalmol, 113:325-332; Mar. 1995.

Hitzenberger et al., "Interferometric Measurement of Corneal Thickness With Micrometer Precision", American Journal of Ophthalmology, 118:468-476, Oct. 1994.

Hitzenberger, C., et al., "Retinal layers located with a precision of 5 µm by partial coherence interferometry", SPIE, 2393:176-181, 1995.

Itoh et al., "Absolute measurements of 3-D shape using white-light interferometer", SPIE Interferometry: Techniques and Analysis, 1755:24-28, 1992.

Izatt et al., "Ophthalmic Diagnostics using Optical Coherence Tomography", SPIE Ophthalmic Technologies, 1877:136-144, 1993.

Izatt, J., et al., "Micrometer-Scale Resolution Imaging of the Anterior Eye In vivo With Optical Coherence Tomography", Arch Ophthalmol, 112:1584-1589, Dec. 1994.

Jean, B., et al., "Topography assisted photoablation", SPIE, vol. 3591:202-208, 1999.

Kamensky, V., et al., "In Situ Monitoring of Laser Modification Process in Human Cataractous Lens and Porcine Cornea Using Coherence Tomography", Journal of biomedical Optics, 4(1), 137-143, Jan. 1999.

Lee et al., "Profilometry with a coherence scanning microscope", Applied Optics, 29(26), 3784-3788, Sep. 10, 1990.

Lubatschowski, "The German Ministry of Research and education funded this OCT guided fs laser surgery in Sep. 2005", http://www.laser-zentrum-hannover.de/download/pdf/taetigkeitsbericht2005.pdf.

Massow, O., et al., "Femotosecond laser microsurgery system controlled by OCT", Laser Zentrum Hannover e.V., The German Ministry of education and research,19 slides, 2007.

Puliafito, Carmen, "Final technical Report: Air Force Grant #F49620-93-I-03337(1)" dated Feb. 12, 1997, 9 pages.

Ren, Q., et al., "Axicon: A New Laser Beam Delivery System for Corneal Surgery", IEEE Journal of Quantum Electronics, 26(12):2305-2308, Dec. 1990.

Ren, Q., et al., "Cataract Surgery with a Mid-Infrared Endo-laser System", SPIE Ophthalmic Technologies II, 1644:188-192, 1992.

Thompson, K., et al., "Therapeutic and Diagnostic Application of Lasers in Ophthalmology", Proceedings of the IEEE, 80(6):838-860, Jun. 1992.

Thrane, L, et al., "Calculation of the maximum obtainable probing depth of optical coherence tomography in tissue", Proceedings of SPIE, 3915:2-11, 2000.

Wisweh, H., et al., "OCT controlled vocal fold femtosecond laser microsurgery", Laser Zentrum Hannover e.V., The German Ministry of education and research, Grants: 13N8710 and 13N8712; 23 slides, 2008.

* cited by examiner

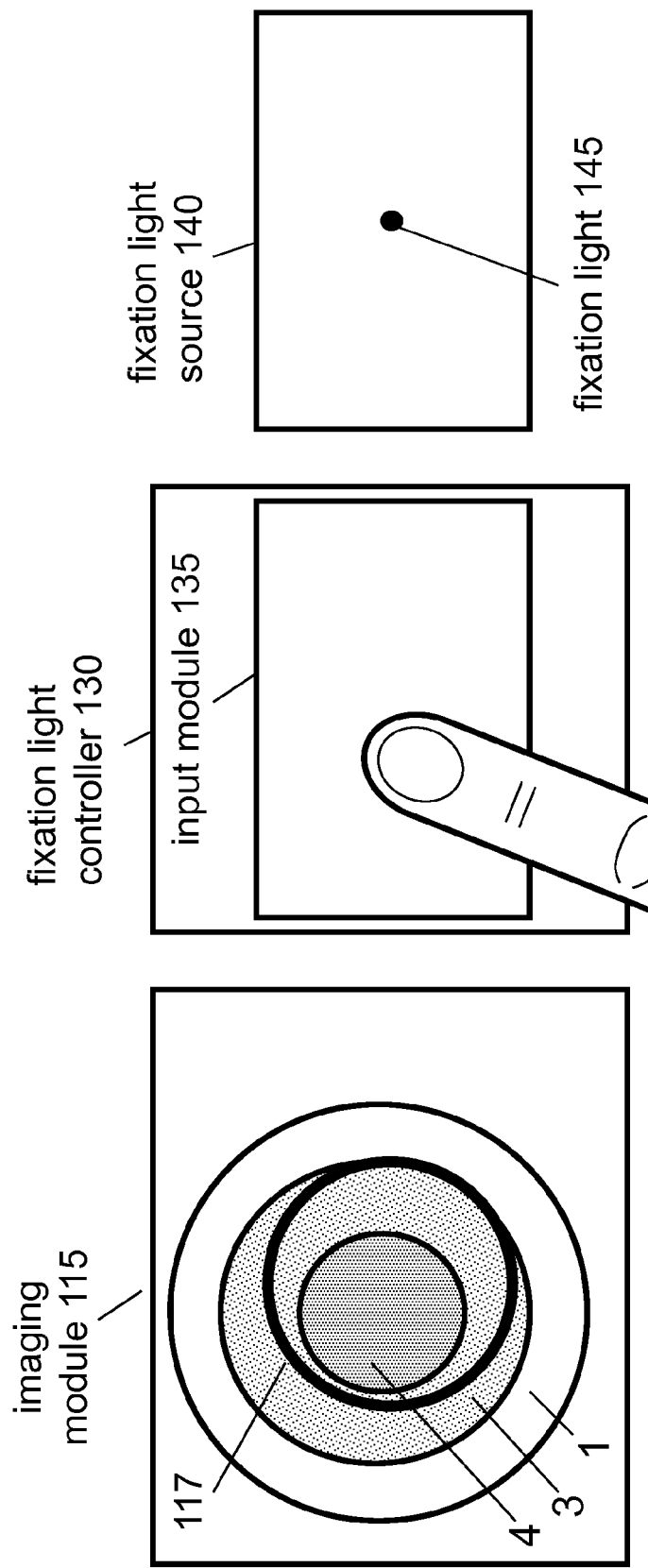

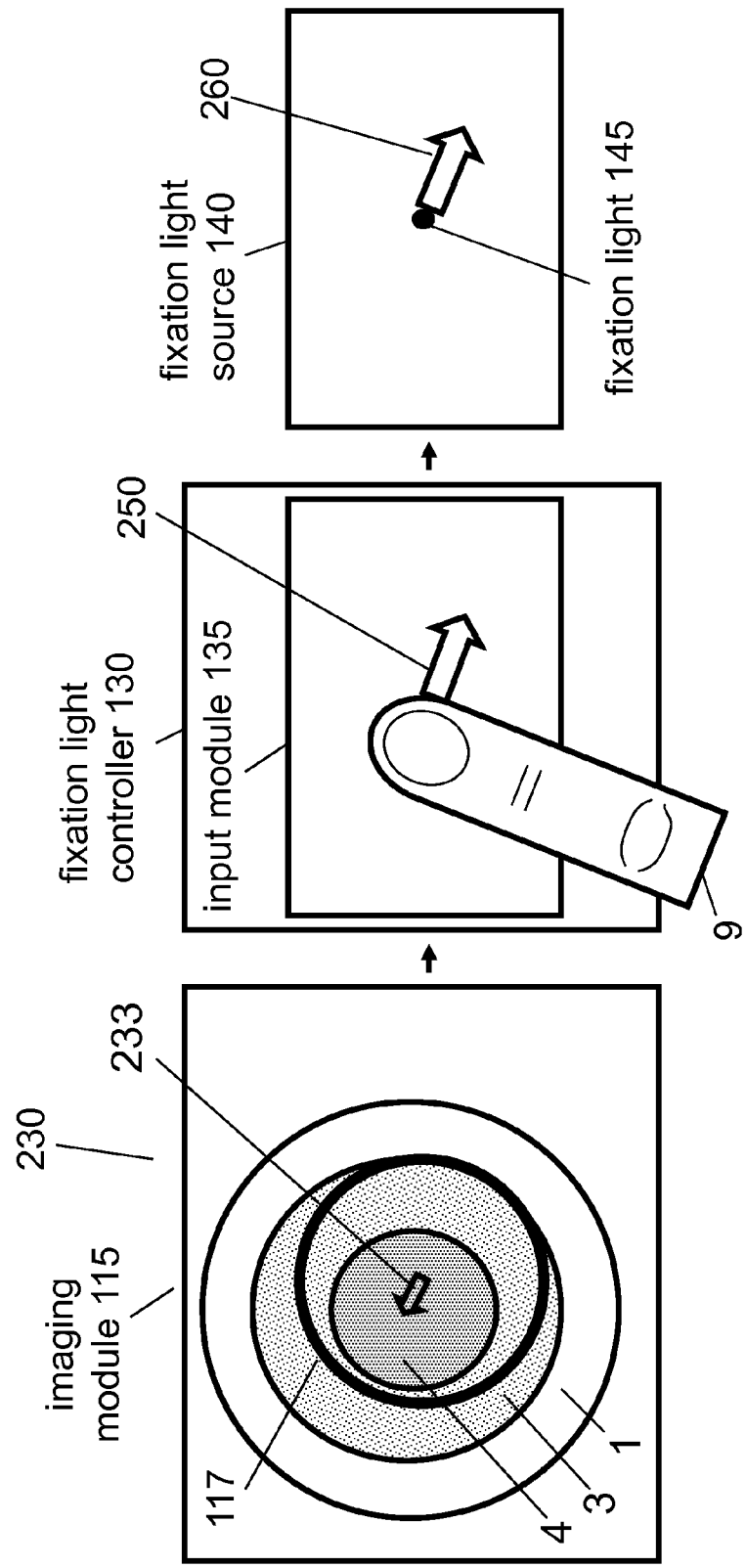

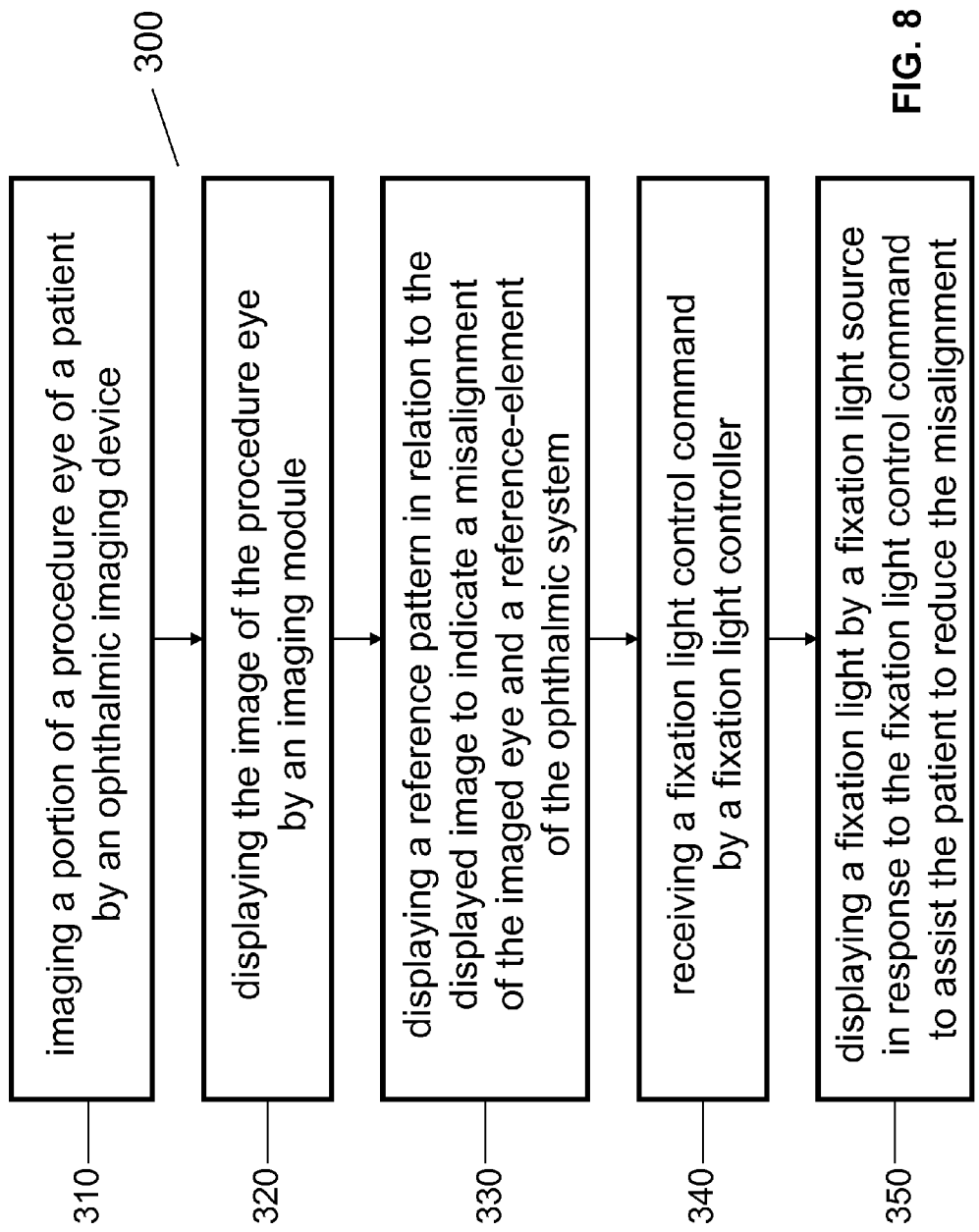

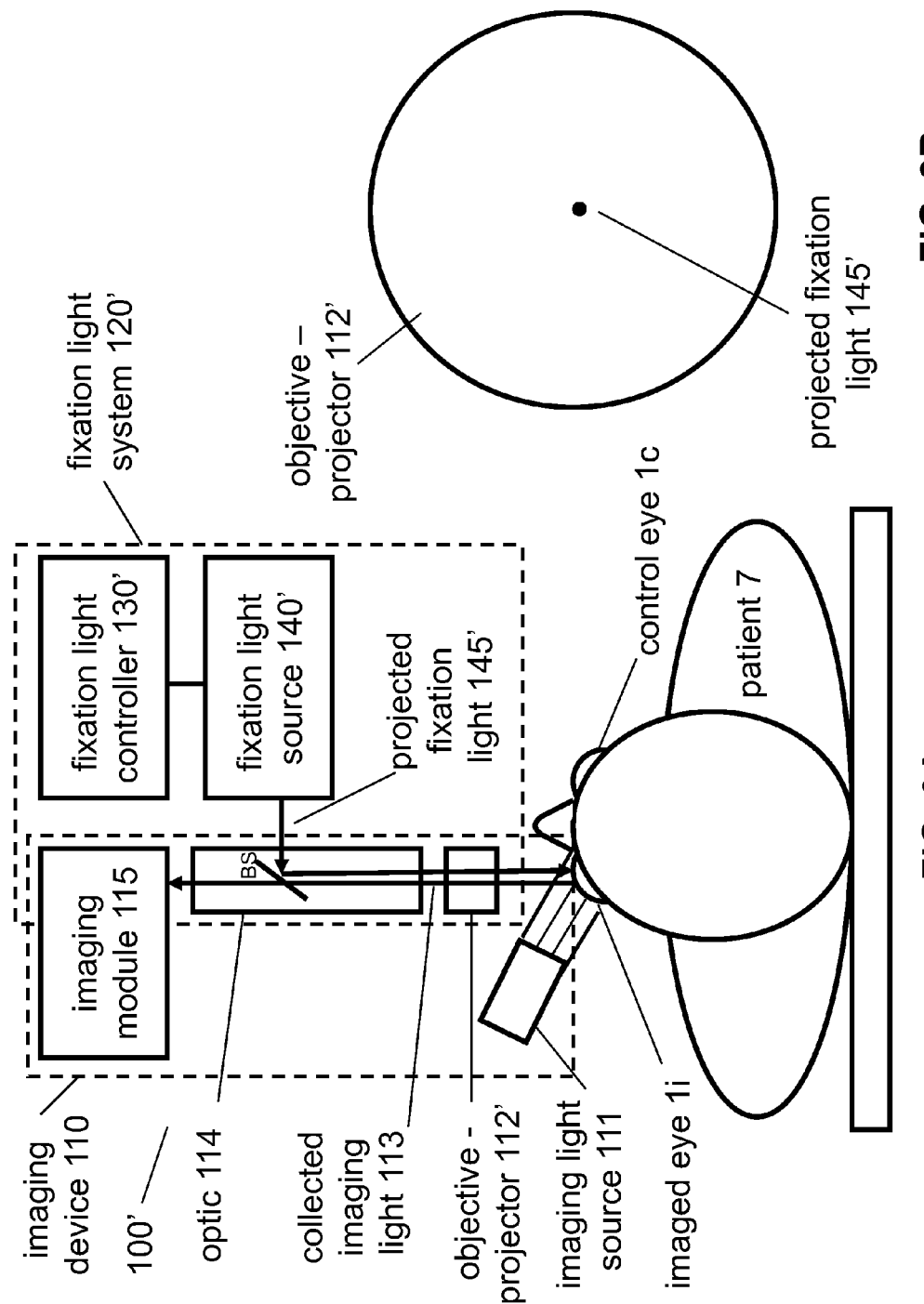

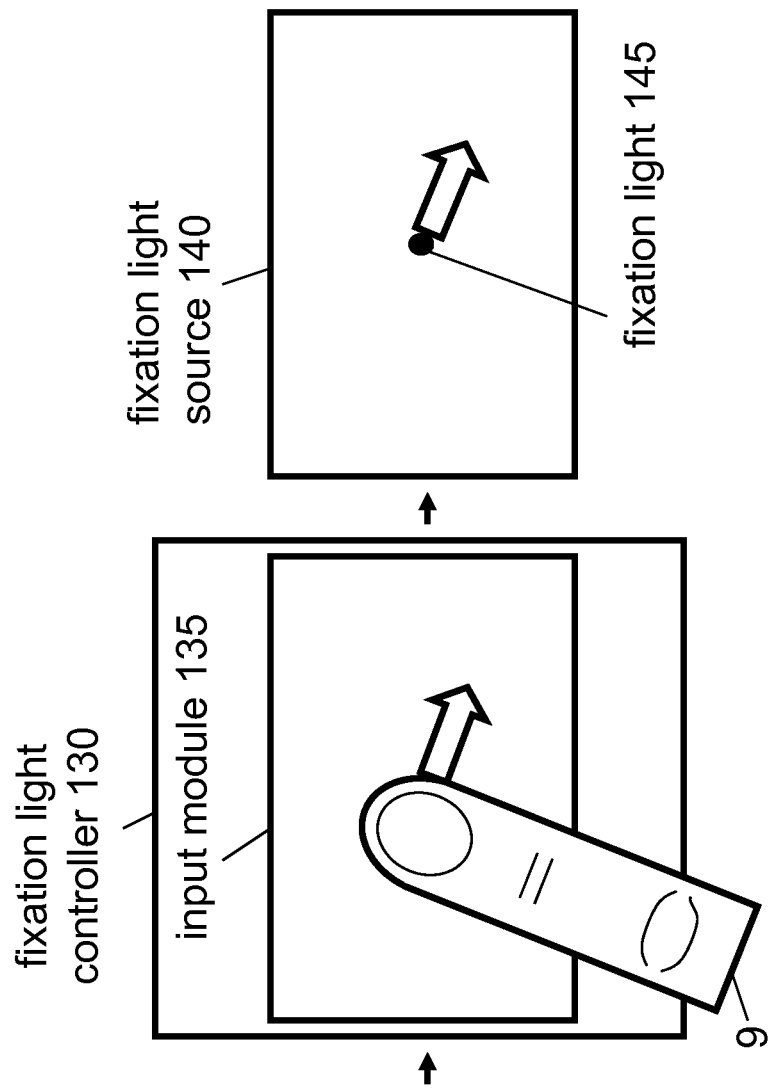

ELECTRONICALLY CONTROLLED FIXATION LIGHT FOR OPHTHALMIC IMAGING SYSTEMS

TECHNICAL FIELD

This patent document relates to systems and techniques for ophthalmic imaging. In more detail, the patent document relates to systems and methods for providing an electronically controlled fixation light for improving a precision of docking of an ophthalmic imaging system to a patient's eye.

BACKGROUND

A variety of advanced imaging devices have been developed over the years for ophthalmic imaging, diagnostics and surgery. For some applications, these imaging devices perform best when their optical axis is aligned with the optical axis of the imaged eye. Once the eye is brought into a position aligned with the optical axis of the imaging device, some devices enhance the precision of the imaging by keeping the eye essentially immobilized in this aligned position with a patient interface of an eye-docking system. The alignment of the optical axes is typically achieved by orienting the eye so that its optical axis is parallel to that of the imaging system and then docking the patient interface on the eye in a concentric manner. Therefore, as the precision of the imaging devices improves, the demand for eye-docking systems which provide more precise alignment also increases.

Achieving good alignment can be challenging, however, as without feedback and guidance systems the patient module often ends up docking to the eye in an off-center position with the eye's optical axis tilted relative to that of the imaging system.

In some systems, the operator of the imaging device can improve the alignment by adjusting the imaging system, the patient's eye, or both during the docking process. The operator can direct the docking iteratively by directing the patient verbally, manually orienting the eyeball, or adjusting portions of the imaging device, such as its objective or gantry. However, the inaccuracy of these approaches can make the docking process quite time consuming and frustrating.

In some systems, such as in some surgical systems using excimer lasers, the alignment is aided by a fixation light. The fixation light can be centered with the optical axis of the imaging system. The patient can be instructed to train his eye on the fixation light, aligning the patient's eye. However, even these fixation light systems have limitations.

SUMMARY

This patent document discloses fixation light controller systems with improved functionalities. In some systems, the fixation light is simply centered with the optical axis of the imaging device. In such systems, in the typical case of the center of the imaged eye being off the optical axis of the imaging device, even if the patient looks at the fixation light, his or her eye will not be properly aligned with the optical axis of the device.

In some systems, including some YAG lasers and slit lamps, the fixation light is not fixed and thus can be manually adjusted. However, since the adjustment is only mechanical, typically it lacks precision. In addition, such mechanical adjustments can still be quite time consuming and frustrating because of their limited precision. The just described lack of precision of some systems can hinder the performance of these devices, including ophthalmic surgical, imaging and diagnostic systems.

The present patent document discloses fixation light controller systems that offer solutions for the above described problems. The disclosed examples and implementations can control a fixation light for an ophthalmic imaging system by non-mechanical control systems. For example, an ophthalmic system can include an ophthalmic imaging device that generates an image of a portion of an imaged eye, a fixation light controller, including an input module, configured to receive an input in relation to the image generated by the ophthalmic imaging device, and a control signal generator that generates a fixation light control signal in response to the received input, and a fixation light source, configured to receive the fixation light control signal and to generate a fixation light according to the received fixation light control signal.

In some implementations, where the ophthalmic imaging device is configured to generate the image essentially optically, the ophthalmic imaging device can include a microscope, an ophthalmic microscope, or a stereo microscope. In some implementations, where the ophthalmic imaging device is configured to generate the image at least in part electronically, the ophthalmic imaging device can include an electronic sensing system that senses a collected imaging light from the imaged eye, including at least one of Charge-Coupled Device (CCD) array, a Complementary Metal-Oxide Semiconductor (CMOS) array, a pixel-array, and an electronic sensor array. The ophthalmic imaging device can also include an electronic display system that displays the image of a portion of the imaged eye in relation to the sensed collected imaging light, including at least one of a Light Emitting Diode (LED) display, a plasma screen, an electronic display, a computer display, a Liquid Crystal Display (LCD) screen, a Cathode Ray Tube (CRT) display, a video-module, a video microscope display, a stereo video microscope display, a high definition (HD) video microscope, a processor-based image system, and an opto-mechanical projector. In some implementations, the ophthalmic imaging device can include an optical coherence tomographic (OCT) imaging system.

In some implementations, the ophthalmic imaging device can include an imaging module, configured to indicate a misalignment of the imaged eye and a reference-component of the ophthalmic imaging device. In some implementations, the reference-component of the imaging device can be an objective, a patient module, a docking tip, an interface, a contact lens, a pupil, a viewing frame, a reference frame, or an internal lens of the ophthalmic system. The imaging module can be configured to display a reference pattern related to the reference-component that can assist a system operator to estimate the misalignment of the imaged eye and the reference-component of the imaging device.

In some implementations, the ophthalmic imaging device can include an image-processor, configured to analyze the image of the portion of the imaged eye and the reference pattern, and to determine the misalignment of the imaged eye and the reference-component of the imaging device, and the image module is configured to display an indication of the misalignment, determined by the image-processor.

In some implementations, the input module is configured to receive an electronic, mechanical, optical, or sensed input. The input module can include a touch-pad, a touch-screen, a joystick, an electro-mechanical sensor, a position sensor, an optical sensor, a voice-prompted actuator, or an electro-mechanical controller. In some implementations, the fixation light source can include at least one of a LED array, a plasma screen, an electronic display, a computer display, an LCD screen, a video-module, an opto-mechanical projector, a CRT display, a slit-lamp, a processor-based image system, and a light-source movable by an electro-mechanical actuator.

In some implementations, the fixation light source is configured to display the fixation light for a non-imaged eye of the patient, and to move the displayed fixation light according to the received fixation light control signal to assist a reduction of a misalignment between the imaged eye and a reference-component of the ophthalmic system. In some implementations, the fixation light source is configured to generate the fixation light for the imaged eye, and to adjust the generated fixation light according to the received fixation light control signal to assist a reduction of a misalignment between the imaged eye and a reference-component of the ophthalmic system.

In some implementations, a method of aligning an eye with an ophthalmic system can include providing an imaging device and an electronically adjustable fixation light system, positioning a component of the imaging device and an imaged eye of a patient for generating an image of a portion of the imaged eye, imaging a portion of the imaged eye, determining a misalignment of the imaged eye relative to the imaging device based on the image, and controlling a fixation light of the fixation light system with an electronic control signal in accordance with the determined misalignment.

In some implementations, the providing the imaging device can include providing a microscope, an ophthalmic microscope, a stereo microscope, a video microscope, a Light Emitting Diode (LED) display, a plasma screen, an electronic display, a computer display, a Liquid Crystal Display (LCD) screen, a Cathode Ray Tube (CRT) display, a video-module, a video microscope display, a stereo video microscope display, a high definition (HD) video microscope, a processor-based image system, or an opto-mechanical projector. In some implementations, the providing the imaging device can include providing an optical coherence tomographic (OCT) system.

In some implementations, the positioning the component of the imaging device can include positioning at least one of an objective, a patient module, a docking tip, a contact lens, a pupil, a viewing frame, a reference frame, and an internal lens of the ophthalmic system in a spatial relation with a structure of the imaged eye suitable for imaging. In some implementations, the determining the misalignment can include determining at least one of a lateral misalignment and a rotational misalignment.

In some implementations, the determining the misalignment can include determining the misalignment with a passive assistance of the imaging device, the imaging device displaying an image of a portion of the imaged eye and a reference pattern. In some implementations, the determining the misalignment can include determining the misalignment with an active assistance of the imaging device, the imaging device displaying an image of a portion of the imaged eye, a reference pattern and a misalignment indicator.

In some implementations, the controlling the fixation light can include generating the electronic control signal with a fixation light controller, wherein the fixation light controller can include a touch-pad, a touch-screen, a joystick, an electro-mechanical sensor, a position sensor, an optical sensor, a voice-prompted actuator, or an electro-mechanical controller. In some implementations, the generating the electronic control signal can include generating the electronic control signal to cause a fixation light source to generate the fixation light to guide the patient to reduce the determined misalignment.

In some implementations, the fixation light source can be a LED array, a plasma screen, an electronic display, a computer display, an LCD display, a CRT display, a video-module, a slit-lamp, a processor-based image system, or a light-source movable by an electro-mechanical actuator. In some implementations, the generating the electronic control signal can include generating the electronic control signal for at least one of the imaged eye and a non-imaged eye. In some implementations, the determining the misalignment and the controlling the fixation light can be repeated iteratively.

In some implementations, a method of aligning an eye with an ophthalmic system can include imaging a portion of a procedure eye of a patient by an ophthalmic imaging device, displaying the image of the procedure eye by an imaging module, displaying a reference pattern in relation to the displayed image to indicate a misalignment of the imaged eye and a reference-element of the ophthalmic system, receiving a fixation light control command by a fixation light controller, and displaying a fixation light by a fixation light source in response to the fixation light control command to assist the patient to reduce the misalignment.

In some implementations, the receiving the fixation light control command can include receiving the fixation light control command through at least one of a touch-pad, a touch-screen, a joystick, an electro-mechanical sensor, a position sensor, an optical sensor, a voice-prompted actuator, and an electro-mechanical controller. In some implementations, the displaying the fixation light can include displaying the fixation light by at least one of a LED array, a plasma screen, an electronic display, a computer display, an LCD screen, a video-module, an opto-mechanical projector, a slit-lamp, a processor-based image system, and a light-source movable by an electro-mechanical actuator. In some implementations, the displaying the fixation light can include displaying the fixation light for one of the procedure eye or the non-procedure eye.

BRIEF DESCRIPTION OF THE DRAWINGS

FIGS. 5A-C illustrate an imaging interface of the imaging module 115, a fixation light controller 130 and a fixation light source 140.

FIGS. 7A-D illustrate an implementation of the method of FIG. 6.

FIG. 8 illustrates a method 300 of aligning an eye with an ophthalmic imaging system.

FIGS. 9A-B illustrate a single optical path implementation of a surgical ophthalmic system 100'.

FIGS. 11A-D illustrate an operation of the ophthalmic system 100" of FIG. 10.

DETAILED DESCRIPTION

Figure 1:
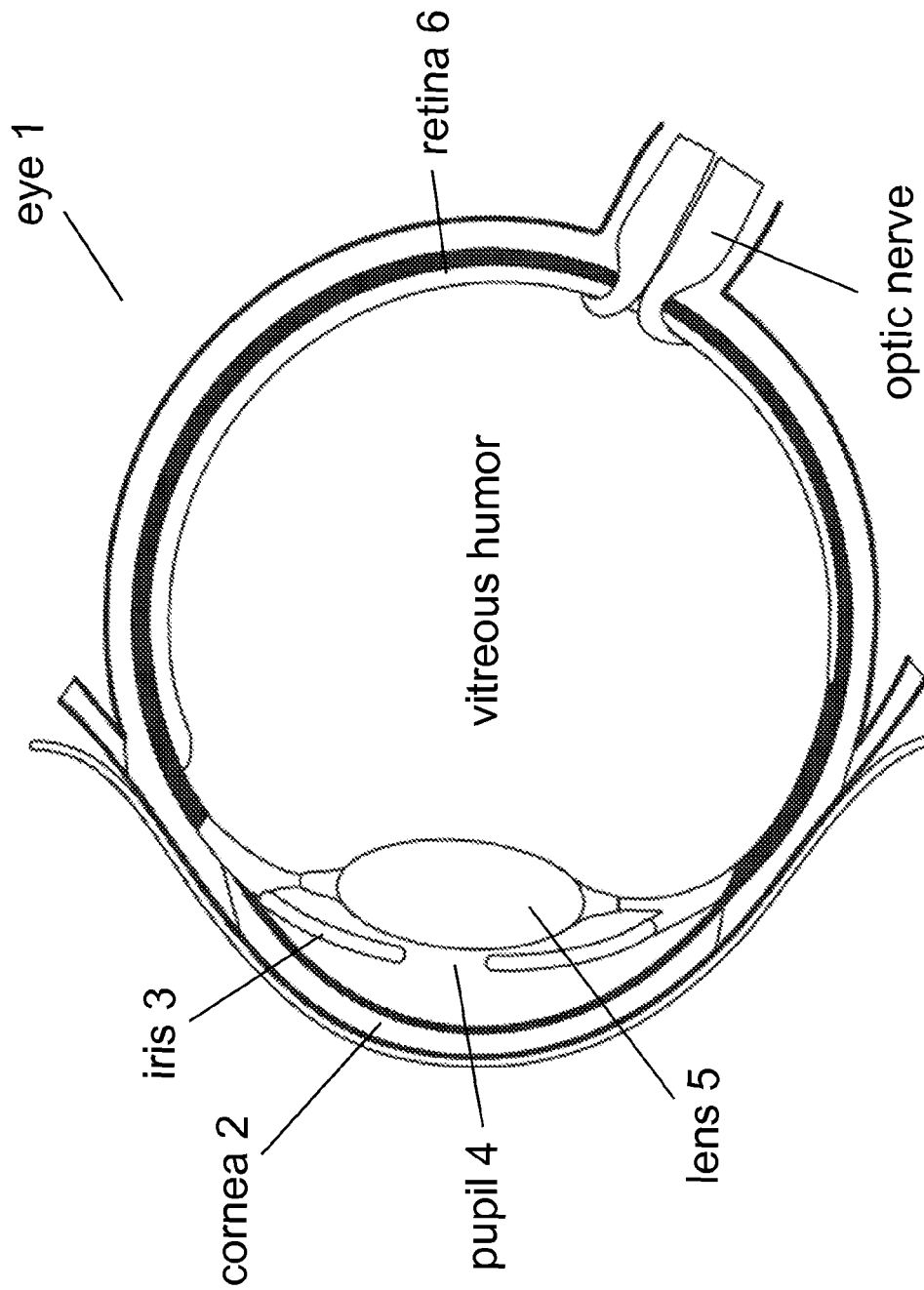
FIG. 1 illustrates a human eye.

FIG. 1 illustrates a human eye 1 in some detail. The eye 1 includes a cornea 2 that receives and refracts the incoming light, an iris 3, a pupil 4 that provides an opening for the light to enter the inner eye, and a lens 5 that focuses the light on the retina 6.

Implementations and embodiments in this patent document provide a fixation light system for ophthalmic imaging devices for increasing the precision of the alignment of the imaged eye and the imaging device.

Figure 2:
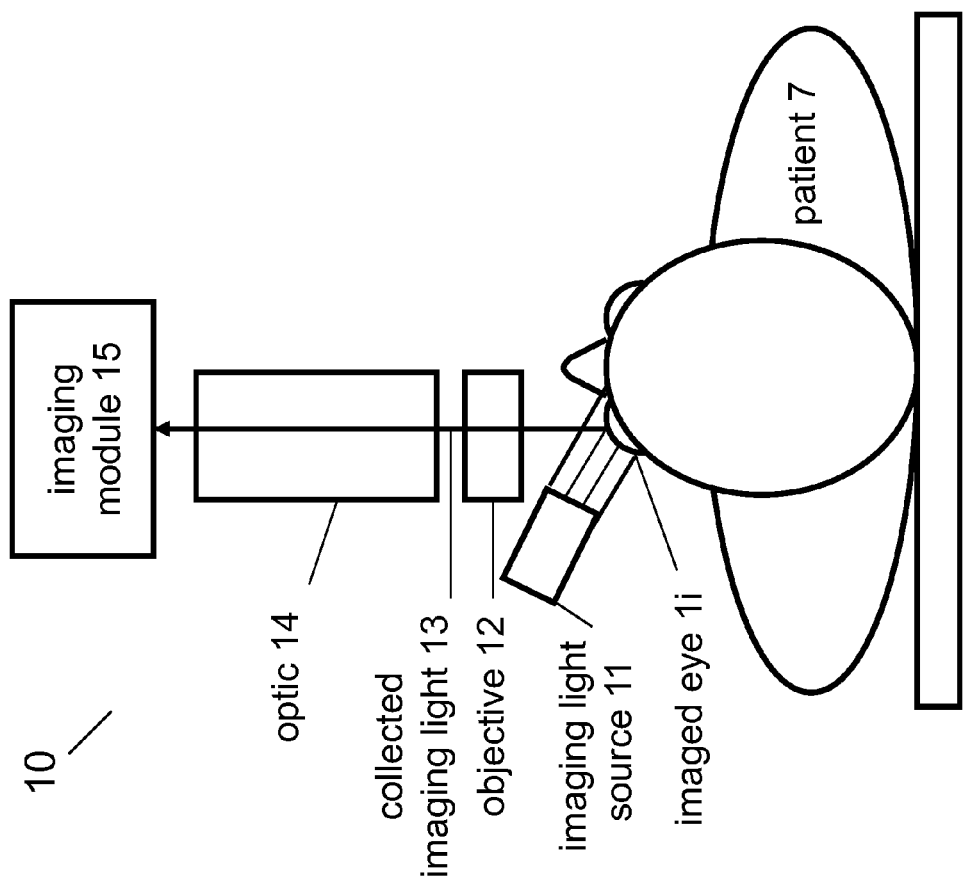
FIG. 2 illustrates an ophthalmic imaging apparatus.

FIG. 2 illustrates an ophthalmic imaging system 10 and its operation. A patient 7 can be laid on a supporting bed. An imaging light source 11 can shine an imaging light on an imaged eye 1i. A portion of the imaging light reflected by the imaged eye 1i can be collected by an objective 12 and guided as a collected imaging light 13 to an optic or optical system 14. The optic 14 can guide the collected imaging light 13 to an imaging module 15. A surgeon or medical professional can analyze the image provided by the imaging module 15 and give instructions to the patient to move the imaged eye 1i to improve its alignment with an optical axis of the imaging system 10. In other cases, the surgeon can manipulate the imaged eye 1i manually to improve the alignment. These steps can be practiced to prepare the imaged eye 1i for docking a patient interface to it. Such patient interfaces can be used for simply imaging the eye 1i, or for performing an ophthalmic surgical procedure. In other systems, a non-contact imaging procedure can be performed after the alignment. In yet other systems, the alignment can be followed by a diagnostic procedure. However, the ophthalmic imaging system 10 can not provide the surgeon with an image of sufficiently high precision because the alignment it provides is only approximate, limiting its accuracy.

Figure 3A:
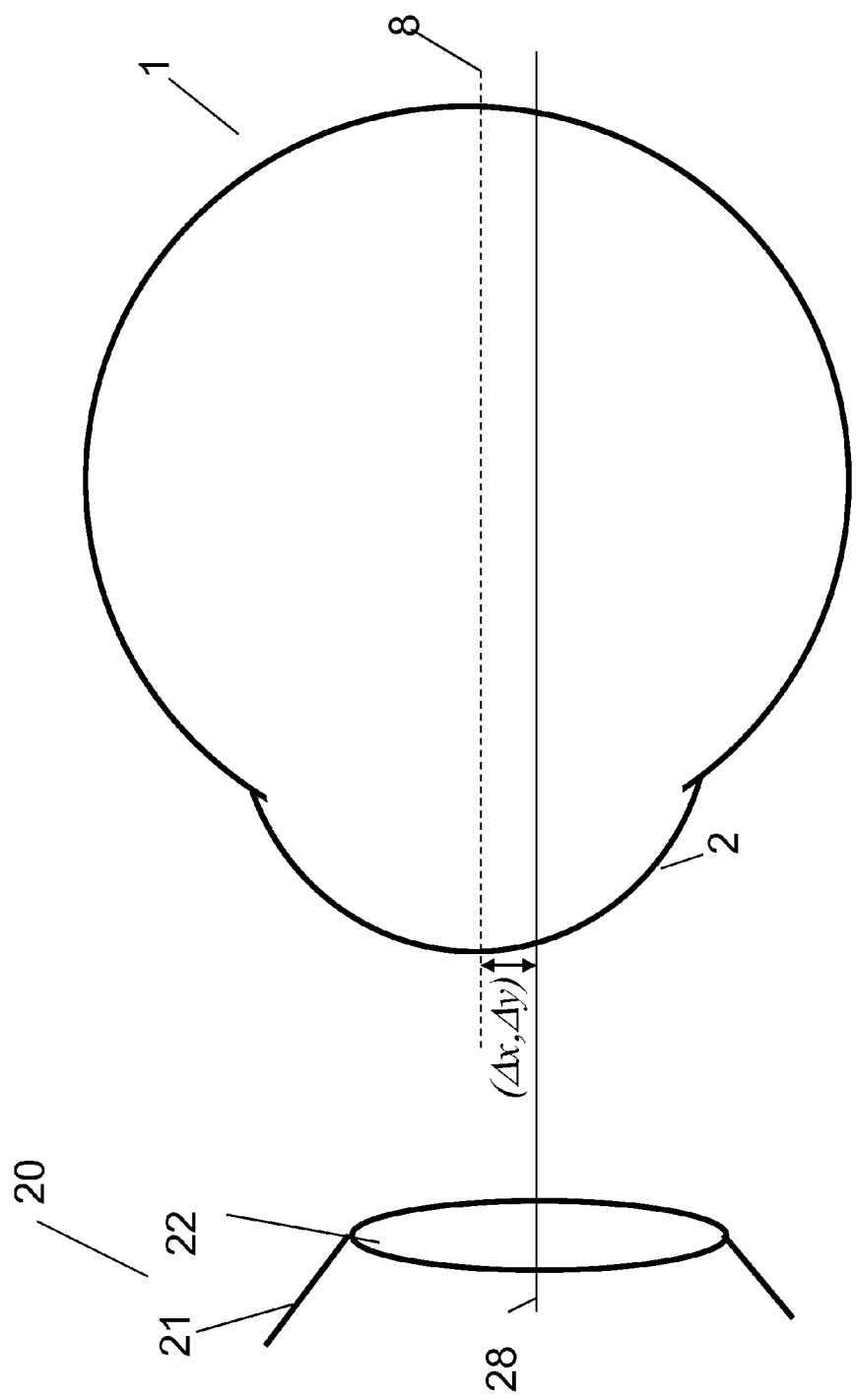
FIGS. 3A-C illustrate various misalignments of an eye and an objective.
Figure 3B:
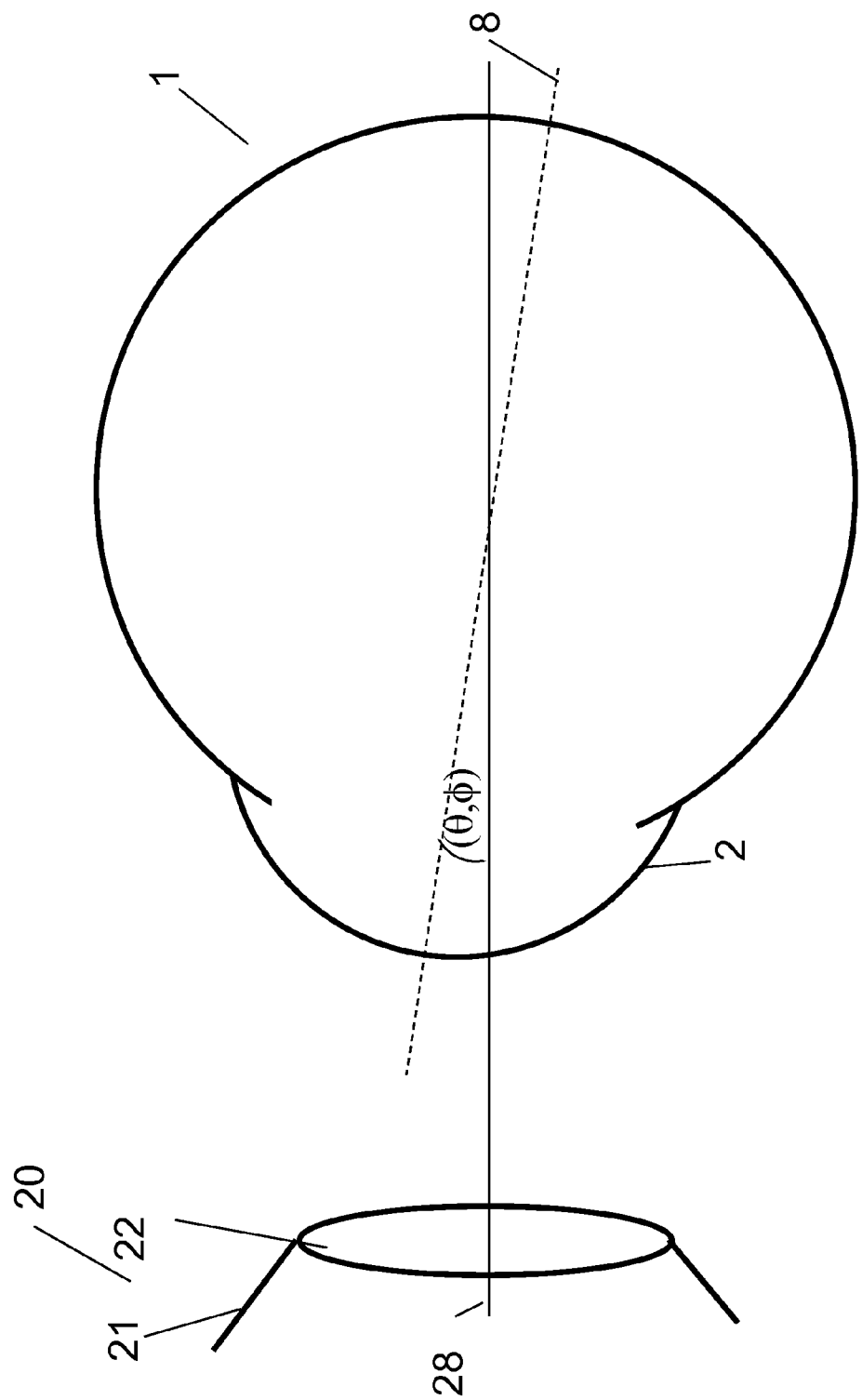

FIGS. 3A-B illustrate that after the use this limited precision ophthalmic imaging system 10, a residual misalignment between the eye 1 and the ophthalmic imaging system 10 can persist. In detail, a distal end 20 of the ophthalmic system 10 can be the objective 12, or a contact module, a docking unit, a distal tip, an interface, or an applanation module. In any of these designs, the distal end 20 can include a housing 21 that supports a distal lens 22. An optical axis 28 of the ophthalmic imaging system 10, typically shared with an optical axis of the distal lens 22, can remain misaligned with an optical axis 8 of the eye 1 even after the above limited-precision docking procedure has been performed.

FIG. 3A illustrates that the misalignment can be a lateral misalignment characterized by a ($\Delta x, \Delta y$) vector between the optical axes 8 of the eye and the optical axis 28 of the objective 12, lying approximately in the lateral plane perpendicular to the optical axis 28.

FIG. 3B illustrates that the misalignment can also be a rotational misalignment. In general, the rotational misalignment can be characterized by the ($\theta, \phi$) Euler angles between the optical axis 8 of the eye and the optical axis 28 of the objective 12. In many cases, the misalignment can be a combination of a lateral and a rotational misalignment.

Figure 3C:
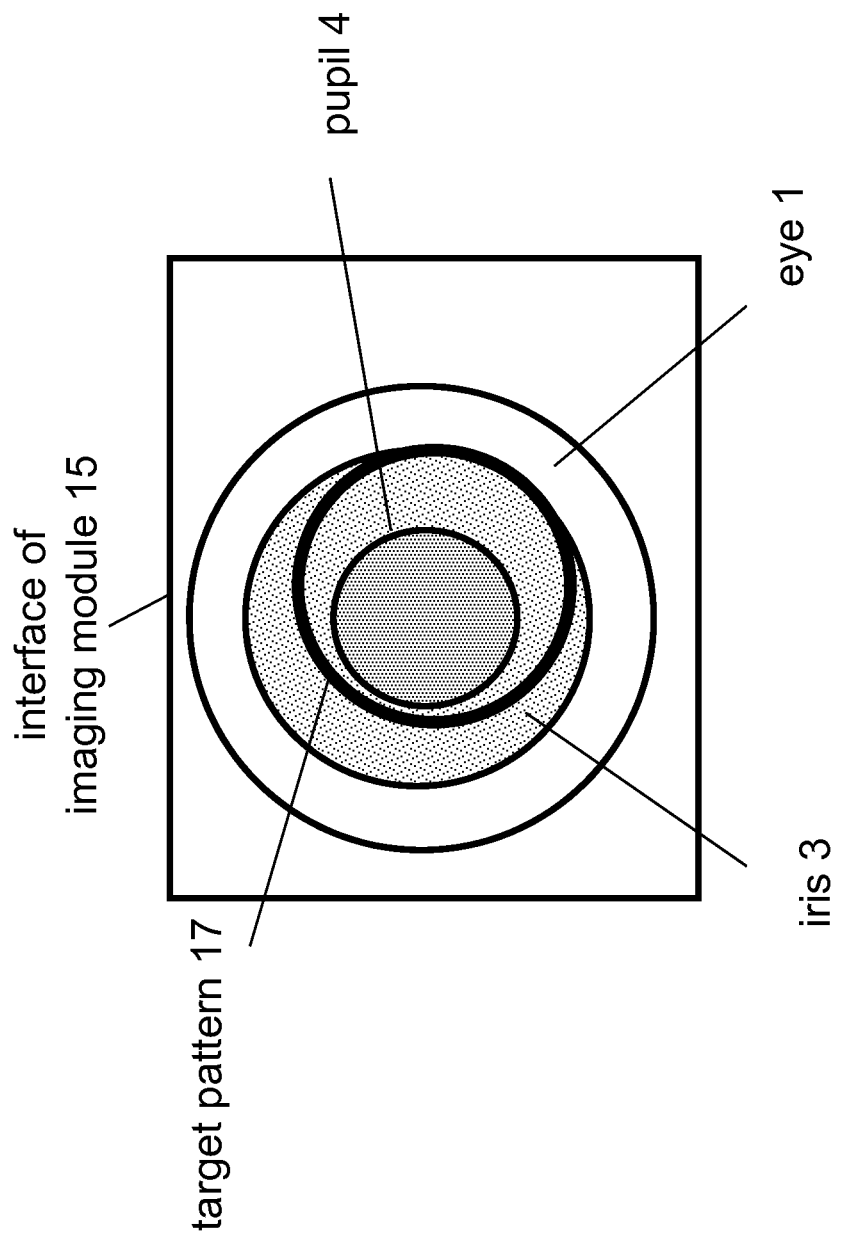

FIG. 3C illustrates that in an imaging interface of the imaging module 15 either misalignment can appear as a displacement of the iris 3 and pupil 4 relative to a targeting pattern 17, such as a target circle. The surgeon can give verbal instructions to the patient to move the imaged eye 1i, or to manipulate the eye 1i manually based on this displayed displacement.

However, verbal instructions can be unclear to an already disoriented patient, and manipulating the eye can be cumbersome and imprecise. Also, the patient is likely to undo or resist the actions of the surgeon or technician.

Some ophthalmic systems can utilize a fixation light to provide guidance for the patient. However, fixation light devices still have shortcomings, as discussed above. Some devices provide adjustable fixation lights as an improvement. However, even in such systems, the location of the fixation light is typically adjusted manually, still resulting in an adjustment process with limited precision.

FIGS. 4-5 illustrate an ophthalmic imaging system 100 that can be used to align the imaged eye 1i and the ophthalmic system 100 with improved precision. The ophthalmic system 100 can include an ophthalmic imaging device 110 and a fixation light system 120.

Figures 4A, 4B:
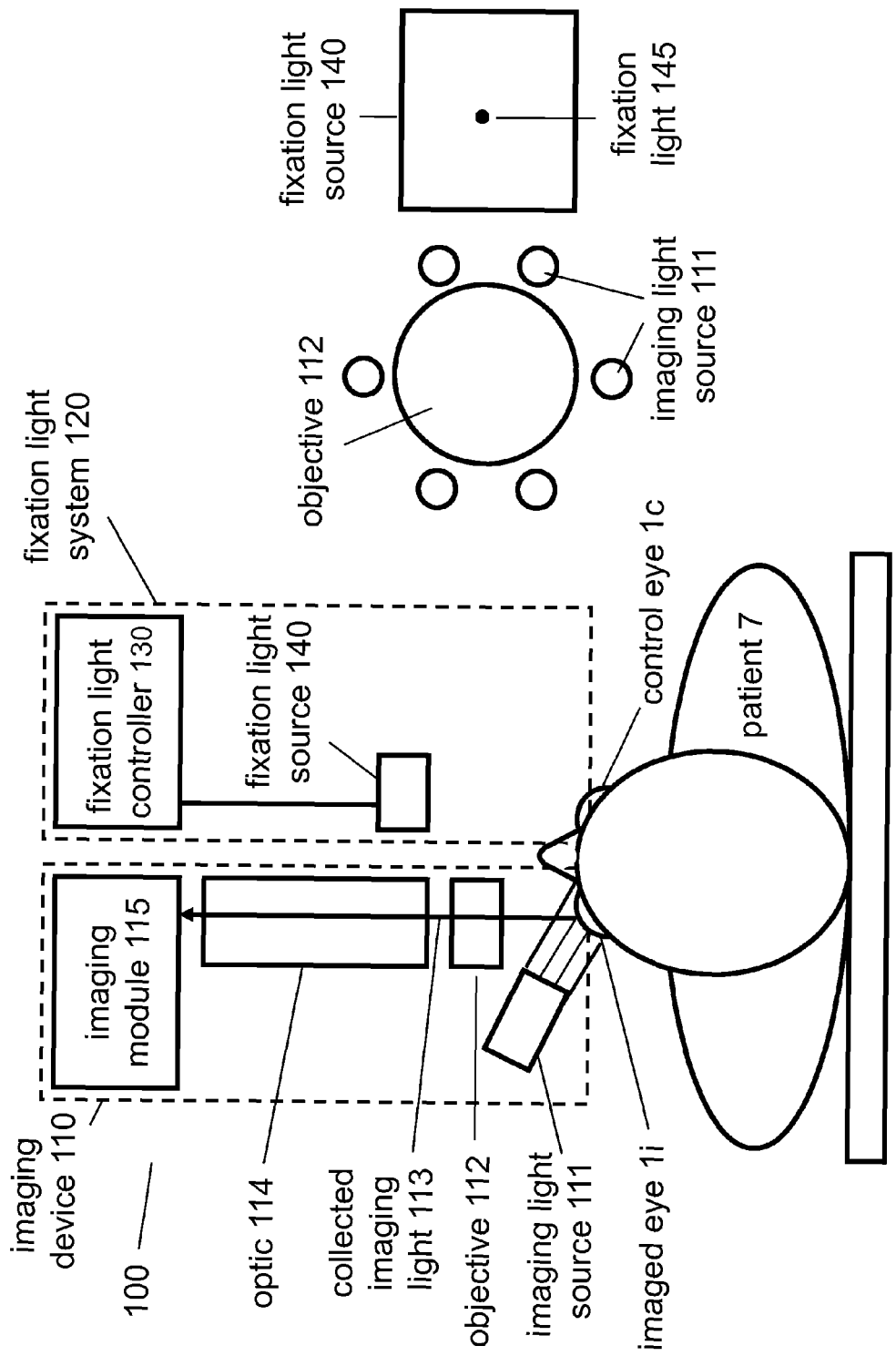
FIG. 4A illustrates an ophthalmic system 100 with a fixation light system 120.
FIG. 4B illustrates a view of an ophthalmic imaging device 110 and the fixation light system 120 as seen by a patient.

FIG. 4A illustrates that the ophthalmic imaging device 110 that can generate an image of a portion of the imaged eye 1i. The ophthalmic imaging device 110 can include an imaging light source 111 that provides an imaging light for the imaged eye 1i. The imaging light source 111 can be a single light, a ring of 4, 6 or 8 lights, or a light source with a continuous ring shape. An objective 112 can collect a fraction of the imaging light, returned by the imaged eye 1i, and direct it as a collected imaging light 113 to an optic 114. The optic 114 can guide the collected imaging light 113 towards an imaging module 115. In general, the optic 114 can be quite complex, including a large number of lenses, and mirrors. The optic can also be multifunctional, for example also configured to guide a surgical laser beam to the imaged eye 1i. The imaging module 115 can provide an image for an operator of the imaging system 100 via an imaging interface.

In some implementations, the ophthalmic imaging device 110 can generate the image essentially optically. For example, the ophthalmic imaging device 110 can include a microscope, an ophthalmic microscope, or a stereo microscope. An imaging interface of these microscopes can include the eyepiece of these microscopes.

In some implementations, the ophthalmic imaging device 110 can generate the image at least in part electronically. For example, the ophthalmic imaging device 110 can include an electronic sensing system that senses the collected imaging light 113. The electronic sensing system can include a Charge-Coupled Device (CCD)-array, a Complementary Metal Oxide Semiconductor (CMOS) array, a pixel-array, or an electronic sensor array to sense the collected imaging light 113.

In these electronic imaging systems the imaging module 115 can include an electronic display system as an imaging interface. This electronic display can display an electronic image of a portion of the imaged eye 1i based on the sensed light 113. This electronic display or imaging interface can be, for example, a Light Emitting Diode (LED) display, a plasma screen, an electronic display, a computer display, a Liquid Crystal Display (LCD) screen, a Cathode Ray Tube (CRT) display, a video-module, a video microscope display, a stereo video microscope display, a High Definition (HD) video microscope, a processor-based image system, an opto-mechanical projector, or a light-source movable by an electro-mechanical actuator. In some implementations, the elements of the optical and the electronic imaging systems can be combined.

Figure 10:
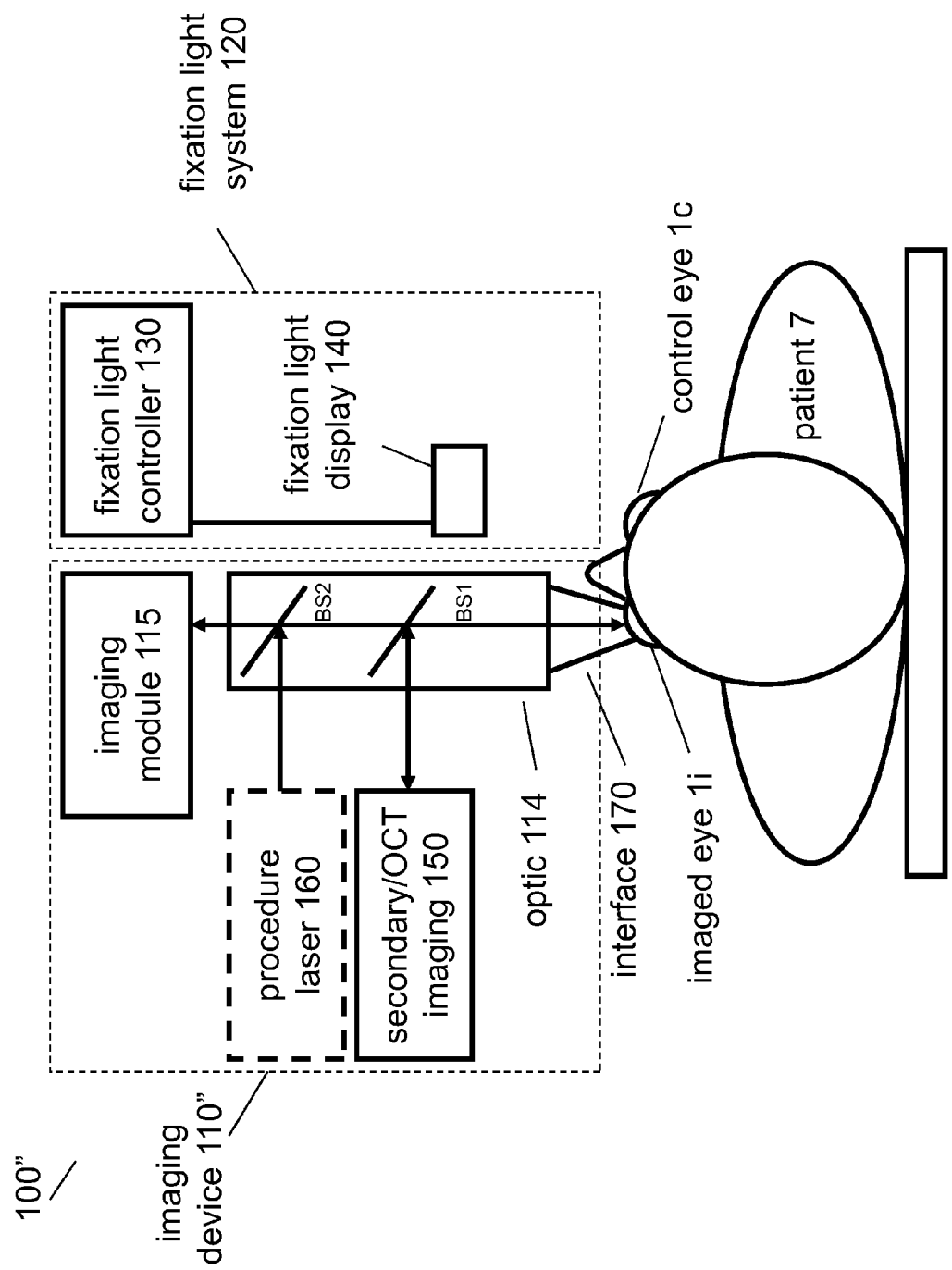
FIG. 10 illustrates an implementation 100" of an ophthalmic system with a surgical ophthalmic apparatus and a fixation light system with a secondary imaging system.

In some implementations, the ophthalmic imaging device can include an optical coherence tomographic (OCT) imaging system, as described in relation to FIGS. 9-10.

FIG. 5A illustrates that the imaging module 115 can indicate a misalignment of the imaged eye 1i and a reference-component of the ophthalmic imaging device 110 by simultaneously displaying an image portion of the imaged eye 1i and a reference or targeting pattern 117, such as a target circle, via its imaging interface.

The reference-component of the imaging device 110 can be an objective, a patient module, a docking tip, an interface, a contact lens, a pupil, a viewing frame, a reference frame, an internal lens of the ophthalmic system, or any equivalents.

The location or display of the targeting pattern 117 can be fixed to the reference-component, in effect indicating the position of the reference-component. Therefore, the simultaneous display of the image portion of the imaged eye 1i and the targeting pattern 117 by the imaging module 115 can effectively assist the determination of the misalignment of the imaged eye 1i.

This assistance can be passive, the imaging module 115 only displaying the image portion of the imaged eye 1i and the reference pattern 117, so that a system operator can determine a degree of the misalignment of the imaged eye 1i and the reference-component of the ophthalmic system 100.

In some implementations, such as in electronic imaging modules 115, the imaging module 115 can actively assist the determination of the misalignment of the imaged eye 1i and the reference-component of the ophthalmic imaging system 100. Such active embodiments can include an image-processor that analyzes the image portion of the imaged eye 1i and the target pattern 117 and computes the misalignment. The image module 115 then can display an indication of the computed misalignment e.g. in the form of an arrow 233 (as shown in FIG. 7A), a numerical indication, a proposed verbal command, or any equivalents.

In addition to the ophthalmic imaging device 110, the ophthalmic imaging system 100 can include the electronically controlled fixation light system 120. This electronically controlled fixation light system 120 can include a fixation light controller 130 and a fixation light source 140.

FIG. 5B illustrates that the fixation light controller 130 can include an input module 135 that can receive an input from a system operator in relation to the image generated by the imaging module 115. For example, a stereo ophthalmic microscope of an optical imaging module 115 can present an image of the iris 3 of the imaged eye 1i in an eyepiece of the stereo microscope and overlay on it a targeting cross hair 117. In another implementation, a video display of an electronic imaging module 115 can display an image of the pupil 4 and a circular target pattern 117 simultaneously, possibly even actively showing an arrow to indicate the misalignment. In either embodiment, an operator of the imaging system 100 can analyze the image portion of the imaged eye 1i and the overlaid targeting pattern 117 to determine a degree of the misalignment of the imaged eye 1i and the ophthalmic system 100.

In response to the determined misalignment, the operator of the imaging system 100 can generate an input or command for the fixation light system 120 through the input module 135 of the fixation light controller 130. This input can represent a command regarding how the imaged eye 1i should be moved to reduce the misalignment, in a manner described below. In an example, if, from the image of the imaging module 115, the operator determined that the center of the imaged eye is 2 millimeters to the right of the center of the objective 112, then the operator can input a command through the input module 135 that will cause the patient to move the imaged eye 2 millimeters to the left to achieve an improved alignment.

The input module 135 can be an electronic, mechanical, optical, or sensed input module. For example, the input module 135 can be a touch-pad, a touch-screen, a joystick, an electro-mechanical sensor, a position sensor, an optical sensor, a voice-prompted actuator, or an electro-mechanical controller.

FIG. 5B illustrates a touch pad embodiment of the input module 135, where the input command is entered by a touching and movement of a finger 9 of a system operator. The movement of the finger 9 can represent a command for the patient how to move the imaged eye 1i to reduce the misalignment with the ophthalmic system 100.

Once the command was entered into the input module 135, a control signal generator of the input module 135 can generate a fixation light control signal in response to the received command. A large variety of well-known electronic signal generators can be utilized for this function.

FIG. 5C illustrates that the fixation light controller 130 can send the generated fixation light control signal to the fixation light source 140. The fixation light source can receive the fixation light control signal and generate or display a fixation light 145 according to the received fixation light control signal.

The fixation light source 140 can include a LED array, a plasma screen, an electronic display, a computer display, an LCD screen, a video-module, an opto-mechanical projector, a slit-lamp, a processor-based image system, or a light-source, movable by an electro-mechanical actuator.

FIG. 4B illustrates that in some implementations the fixation light source 140 can generate and display the fixation light 145 for a non-imaged, or control, eye 1c of the patient 7. The fixation light source 140 can first generate and display the fixation light 145, and then move the displayed fixation light 145 according to the received fixation light control signal. Since the movements of the control eye 1c and the imaged eye 1i closely track each other, as the control eye 1c is moved by the patient according to the displayed fixation light 145, the imaged eye 1i moves in a correlated manner. Because of this correlation between the movements of the imaged eye 1i and the control eye 1c, the fixation light system 120 can assist the reduction of the misalignment of the imaged eye 1i relative to the ophthalmic imaging system 110.

Other embodiments may simply display the fixation light 145 on the fixation light source 140 at a location according to the fixation light control signal, instead of moving it. In either of these embodiments, the patient can be instructed to follow the fixation light 145 with the control eye 1c.

FIG. 4B illustrates the appearance of the ophthalmic system 100 for the patient 7 in some embodiments. The left panel shows that the imaged eye 1i can see the objective 112, surrounded by e.g. six imaging light sources 111. The right panel shows that the non-imaged/control eye 1c can see the fixation light 145 displayed on the fixation light source 140. In this embodiment, the fixation light source 140 can be an LCD screen or an equivalent, and the fixation light 145 can be a bright spot displayed on the dark LCD screen 140.

To facilitate procedures on both eyes, some embodiments may include two fixation light sources 140, one on each side of the objective 112.

Figure 6:
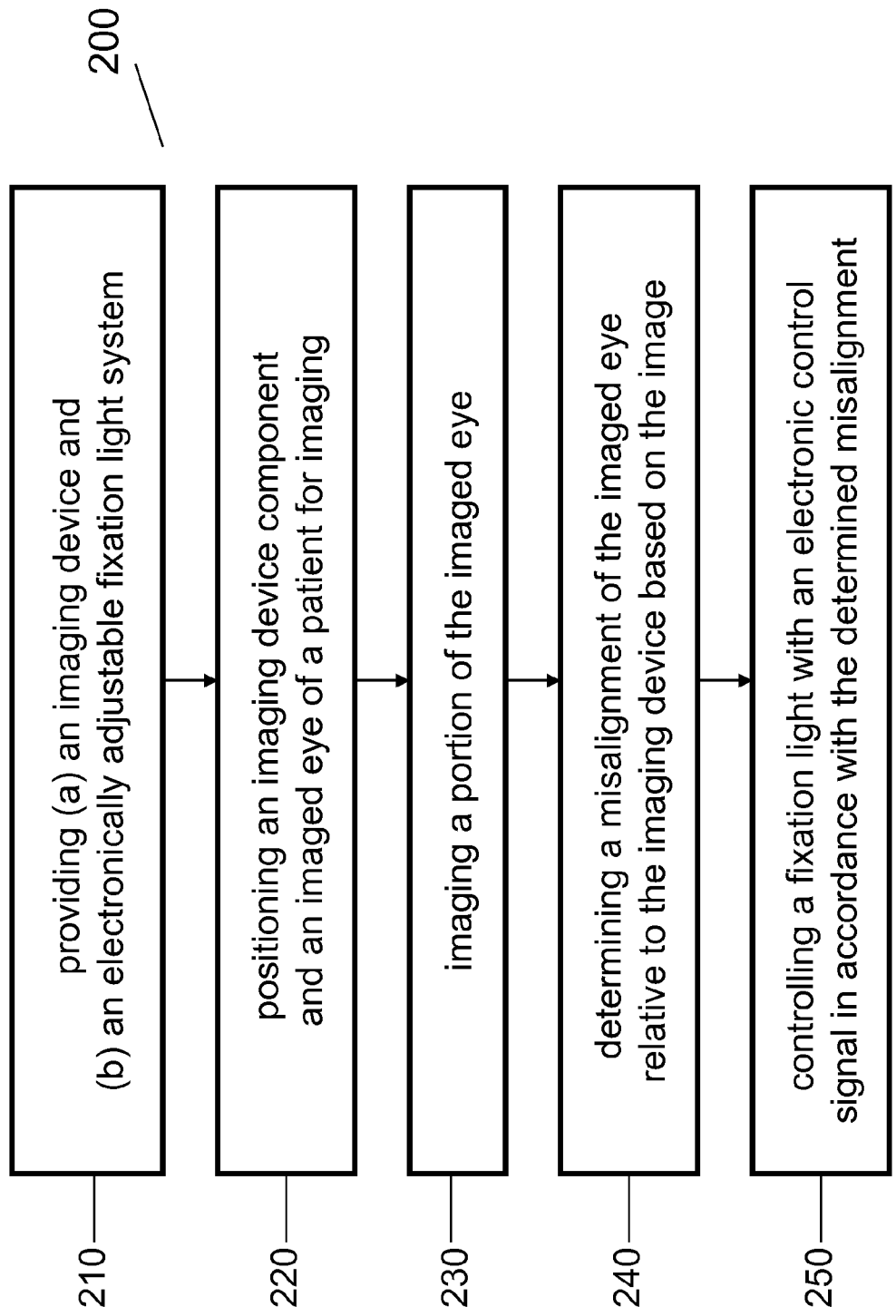
FIG. 6 illustrates a method of operation 200 of the fixation light system.

FIG. 6 illustrates a method 200 for operating the ophthalmic imaging system 100. The method 200 can include providing an imaging device—210a, and an electronically adjustable fixation light system—210*b*; positioning a component of the imaging device and an imaged eye of a patient for imaging—220; imaging a portion of the imaged eye—230; determining a misalignment of the imaged eye and the component of the imaging device—240; and controlling a fixation light electronically according to the determined misalignment—250.

The providing the imaging device 210*a* can include providing a microscope, an ophthalmic microscope, a stereo microscope, a video microscope, a Light Emitting Diode (LED) display, a plasma screen, an electronic display, a computer display, a Liquid Crystal Display (LCD) screen, a Cathode Ray Tube (CRT) display, a video-module, a video microscope display, a stereo video microscope display, a high definition HD video microscope, a processor-based image system, an opto-mechanical projector, or an optical coherence tomographic (OCT) system. In some of these imaging devices 110 the objective 112 can capture the collected imaging light 113 returned by the imaged eye 1*i*. The optic 114 can guide the collected imaging light 113 to the imaging module 115 and display it e.g. by the imaging interface of the imaging module 115.

The providing the electronically adjustable fixation light system 210*b* can include providing the fixation light controller 130 and the fixation light source 140.

The positioning 220 can include positioning at least one of the objective 112, the patient module, the docking tip, the contact lens, the pupil, the viewing frame, the reference frame, or an internal lens of the ophthalmic system to line up with a structure of the imaged eye 1*i*. The positioning 220 can also include moving the imaged eye 1*i* to a position suitable for imaging the imaged eye 1*i*. The positioning can also include moving both the objective 112 of the ophthalmic imaging device 100 and the imaged eye 1*i* to positions suitable for imaging the imaged eye 1*i*.

In some implementations, after the positioning 220 the imaged eye 1*i* and the imaging device 110 can be close but not yet in physical contact. In others, there can be a partial physical contact that still allows for a movement of the imaged eye 1*i* by either the patient of the surgeon.

The imaging a portion of the imaged eye 230 can include the surgeon imaging a portion of the imaged eye 1*i* with at least one of a microscope, an ophthalmic stereo microscope, a video microscope, a stereo video microscope, a high definition (HD) video microscope, or an optical coherence tomographic (OCT) system.

FIG. 7A illustrates that in some implementations the determining the misalignment 240 can include determining at least one of a direction and a magnitude of a lateral misalignment, or an angle of rotation of a rotational misalignment that remained after the positioning 220.

The determining the misalignment 240 can be performed by the operator of the ophthalmic imaging system 100, such as a surgeon. In such implementations, the imaging device 110 can assist the determining 240 passively by displaying an imaged portion of the imaged eye 1*i* and the reference or targeting pattern 117 simultaneously by the imaging interface of the imaging module 115. FIG. 7A illustrates an example where the image of the iris 3 and pupil 4 of the imaged eye 1*i* is overlaid with a display of the targeting circle 117. By analyzing the two overlaid images, the surgeon can determine the misalignment.

In some implementations, the imaging device 110 can assist the determining 240 actively by displaying the imaged portion of the imaged eye 1*i*, the reference or targeting pattern 117, and a computed misalignment indicator 233 by the imaging interface of the imaging module 115. FIG. 7A illustrates an example, where the image of the iris 3 and pupil 4 of the imaged eye 1*i* is shown simultaneously with the targeting circle 117. In addition, the ophthalmic imaging system 100 can determine the magnitude of the misalignment and indicate it by displaying a misalignment indicator arrow 233. The misalignment arrow 233 can, for example, point from the center of the targeting circle 117 to the center of the pupil 4, or to the center of the limbus, as determined by an image processing protocol.

The controlling the fixation light 250 can include generating an electronic control signal according to the determined misalignment. In some implementations, the electronic control signal can be generated by operating at least one of a touch-pad, a touch-screen, a joystick, an electro-mechanical sensor, a position sensor, an optical sensor, a voice-prompted actuator, or an electro-mechanical controller.

The controlling the fixation light 250 can also include generating the electric control signal to cause the fixation light source 140 to display the fixation light 145 to guide the patient to reduce the misalignment between the imaged eye 1*i* and the ophthalmic imaging system 110.

FIG. 7B illustrates that in an example the surgeon may analyze the image of the imaged eye 1*i* and targeting pattern 117 on the imaging module 115 and determine that the pupil of the imaged eye 1*i* is misaligned relative to the targeting pattern 117 in the upper-left direction, using the imaging interface of the imaging module 115 as a reference. The surgeon's determination may be aided by the misalignment indicator 233.

In response, the surgeon can decide that the fixation light 145 should be adjusted or moved to the lower-right direction by the fixation light source 140 to guide the patient to reduce and compensate this misalignment. Correspondingly, the surgeon can create a fixation light control command or input to represent the compensating adjustment of the fixation light 145. In this example, the surgeon can move his finger 9 on a touchpad 135 of the fixation light controller 130 in the lower-right direction. The input of this fixation light control command can lead to the generation of an electronic control signal by the fixation light controller 130 that causes the fixation light source 140 to move the fixation light 145 in the lower-right direction on an LCD screen. In other embodiments, other types of movement of the surgeon's finger can represent the necessary compensating adjustment, such as a movement in the upper-left direction.

FIG. 7C illustrates that in the above example, moving the surgeon's finger 9 in the lower-right direction can cause the fixation light source 140 to correspondingly adjust the display of the fixation light 145 also in the lower-right direction on the LCD screen of the fixation light source 140. The patient can be instructed to follow this adjustment of the fixation light 145 with the non-imaged control eye 1*c*. The movement of the control eye 1*c* is followed or tracked by the movement of the imaged eye 1*i*. Therefore, the method 200 can reduce the misalignment of the imaged eye 1*i* and the ophthalmic imaging device 110.

Figure 7D:
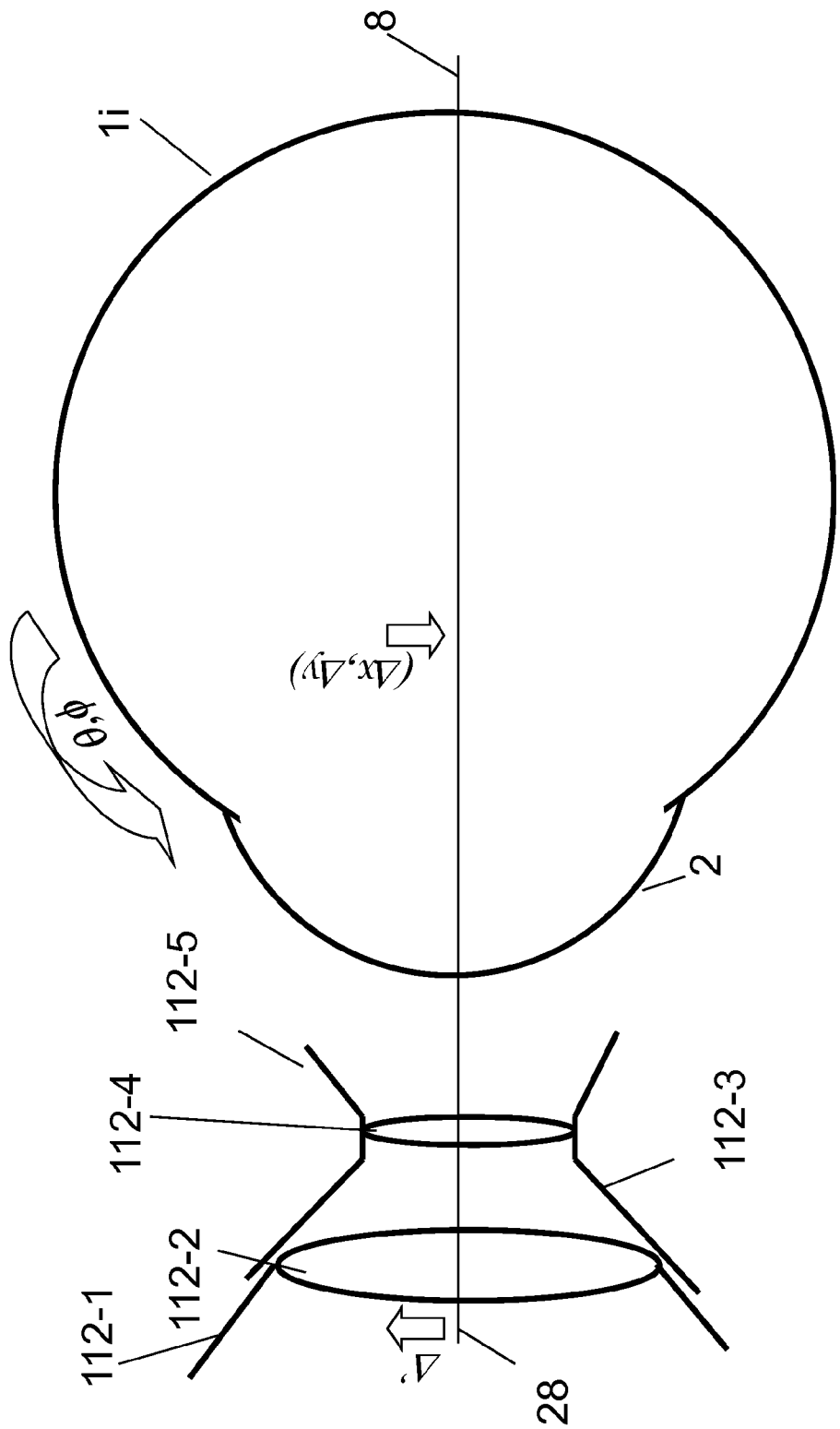

FIG. 7D illustrates some aspects of the misalignment reduction. The objective 112 can include various elements in various implementations. In some examples, the objective 112 can include a housing 112-1 to support a distal lens 112-2. This distal lens 112-2 can be the application tip of the ophthalmic system 100, in some cases directly making contact with the eye. In these embodiments, the above system 100 and method 200 can be used to align the distal lens 112-2 with the imaged eye 1*i*.

In other examples, a possibly disposable patient interface 112-3 can be attached to the objective 112. The patient interface 112-3 can include a contact lens or applanation plate 112-4 and a vacuum skirt or suction seal 112-5. In these embodiments, the above system 100 and method 200 can be used for aligning either the contact lens 112-4 or the distal lens 112-2 with the imaged eye 1$i$.

FIG. 7D illustrates that in any of the above embodiments, the surgeon can enter a misalignment-compensating control command into the fixation light controller 130, generating an electronic control signal that causes the fixation light source 140 to adjust the fixation light 145. The patient can follow the adjusted fixation light 145 with the control eye 1$c$, causing the imaged eye 1$i$ to move accordingly. The surgeon typically enters control commands that will cause the patient to move his imaged eye 1$i$ to reduce the misalignment with the ophthalmic imaging device 110.

A lateral misalignment can be compensated by the patient following the adjusted fixation light 145 to move the imaged eye 1$i$ laterally by $\Delta$, or in general by the misalignment vector ($\Delta x, \Delta y$). In other implementations, the lateral misalignment can be also compensated by the surgeon moving the objective 112 with a lateral adjustment $\Delta'$, or in general by ($\Delta' x, \Delta' y$). In some cases, both the imaged eye 1$i$ and the objective 112 can be adjusted to compensate the lateral misalignment together.

In yet other embodiments, a rotational misalignment can be reduced by the patient following the adjusted fixation light 145 causing the imaged eye to rotate by an angle $\alpha$, or in general by the Euler angles ($\theta, \phi$).

Finally, in some cases both lateral and rotational misalignment can be present between the imaged eye 1$i$ and the ophthalmic system 100. In such cases the surgeon may guide the compensation of the rotational misalignment by adjusting the fixation light 145 and by instructing the patient to follow the fixation light, while laterally moving the objective 112 to compensate the lateral misalignment.

As often the first fixation light control command will result in a reduction of the misalignment but not in its elimination, after the patient reacted to the adjusted fixation light 145, the surgeon can repeat the determining a residual misalignment 240 and the controlling the fixation light with the control signal 250 to further reduce the misalignment iteratively. This iteration can be continued until the misalignment has been compensated with a desired precision.

As before, the fixation light source 140 can include a LED array, a plasma screen, an electronic display, a computer display, an LCD screen, a video-module, a slit-lamp, a processor-based image system, or a light-source movable by an electro-mechanical actuator.

FIG. 8 illustrates a method of operation 300 of the ophthalmic imaging system 100 describing the system's operations.

The method 300 of aligning the imaged eye 1$i$ eye with the ophthalmic system 100 can include imaging a portion of a procedure eye of a patient by an ophthalmic imaging device—310; displaying the image of the procedure eye by an imaging module—320; displaying a reference pattern in relation to the displayed image to indicate a misalignment of the imaged eye and a reference-element of the ophthalmic system—330; receiving a fixation light control command by a fixation light controller—340; and displaying a fixation light by a fixation light source in response to the fixation light control command to assist the patient to reduce the misalignment—350.

The acts 310-330 have been described earlier in detail from the viewpoint of the operator of the ophthalmic system 100, such as the surgeon. The receiving the fixation light control command 340 can include receiving the fixation light control command through at least one of a touch-pad, a touch-screen, a joystick, an electro-mechanical sensor, a position sensor, an optical sensor, a voice-prompted actuator, or an electro-mechanical controller.

The displaying the fixation light 350 can include displaying the fixation light by at least one of a LED array, a plasma screen, an electronic display, a computer display, an LCD screen, a video-module, an opto-mechanical projector, a slit-lamp, a processor-based image system, or a light-source movable by an electro-mechanical actuator.

The displaying the fixation light 350 can include displaying the fixation light for one of the procedure eye or the non-procedure eye.

FIGS. 9A-B illustrate another implementation of the ophthalmic system 100'. The earlier described functionalities of the elements 110-145 can characterize the present implementation of the elements 110-145' as well and will not be repeated here.

In addition, the elements 110-145' can have functionalities related to the feature that in this implementation of the imaging system 100 the fixation light 145' is not displayed via a separate fixation light display or source 140 for the control eye 1$c$. Instead, a fixation light controller 130' can apply an electronic fixation light control signal to a fixation light source 140' that projects a projected fixation light 145' into the optical pathway of the imaging device 110. As such, the imaging device 110 and the fixation light system 120' share some elements, as shown by the dotted lines. In some implementations, the projected fixation light 145' can be coupled into the optic 114 that contains additional adjustable mirrors to adjust the optical path of the projected fixation light 145'. This coupling can take place between the optic 114 and the imaging module 115, or somewhere along the optic 114 e.g. by a beam splitter BS, as shown. In other embodiments, the projected fixation light 145' can have a separate optical train or pathway to adjust its path and can be coupled into the optical pathway of the imaging device 110 just before the objective-projector 112'.

FIG. 9B illustrates that in these implementations the projected fixation light 145' can be projected by the objective-projector 112' into the imaged eye 1$i$. In these embodiments, the patient can be instructed to follow the projected fixation light 145' directly by the imaged eye 1$i$ to reduce the misalignment.

FIG. 10 illustrates another implementation of the ophthalmic system 100". The earlier described functionalities of the elements 110-145 can characterize the present implementation of the elements 110"-145 as well and will not be repeated here.

In addition, the elements 110"-145 can have functionalities related to the feature that the ophthalmic system 100" can include a secondary imaging device 150. The secondary imaging device 150 can be, for example, an optical coherence tomographic (OCT) system. Numerous OCT imaging systems are known, including time-domain OCT systems and frequency domain OCT systems with a spectrometer or a swept source. A wide variety of these OCT systems can be used in the ophthalmic system 100" to achieve various advantages. The imaging beam for the secondary imaging device 150 can be coupled into the main optical pathway via a beam splitter BS1.

Some implementations of the ophthalmic system 100" can also include a procedure laser 160 for various ophthalmic surgical procedures. Further, some embodiments can include a patient interface 170 to provide firmer connection between the imaged eye 1*i* and the ophthalmic imaging device 110, for example with the application of vacuum suction. This patient interface 170 can be analogous to the patient interface 112-3 in FIG. 7D.

In some implementations of the ophthalmic system 100" the imaging can be performed by the imaging module 115, in which case the system 100" and its operation can be largely analogous to the earlier described embodiments.

In other implementations though, the secondary/OCT imaging system 150 can be used to image the imaged eye 1*i*. OCT imaging can be particularly useful to image a structure of the eye that is not visible for an ophthalmic microscope. An example is imaging the lens 5 of the eye. Because of its soft supporting system, the lens 5 is often not concentric with the visible structures of the eye such as the pupil 4. Further, as the weight of the objective 112 pressures the eye through the interface 170, the lens 5 can be additionally displaced and tilted. At the same time, aligning the ophthalmic system 100" with the lens 5 instead of the pupil 4 or the limbus can be particularly important during cataract surgeries where the quality of the capsulotomy and other procedures can be improved by such an alignment.

FIGS. 11A-D illustrate an operation of this implementation of the ophthalmic system 100".

Figures 11A, 11B:
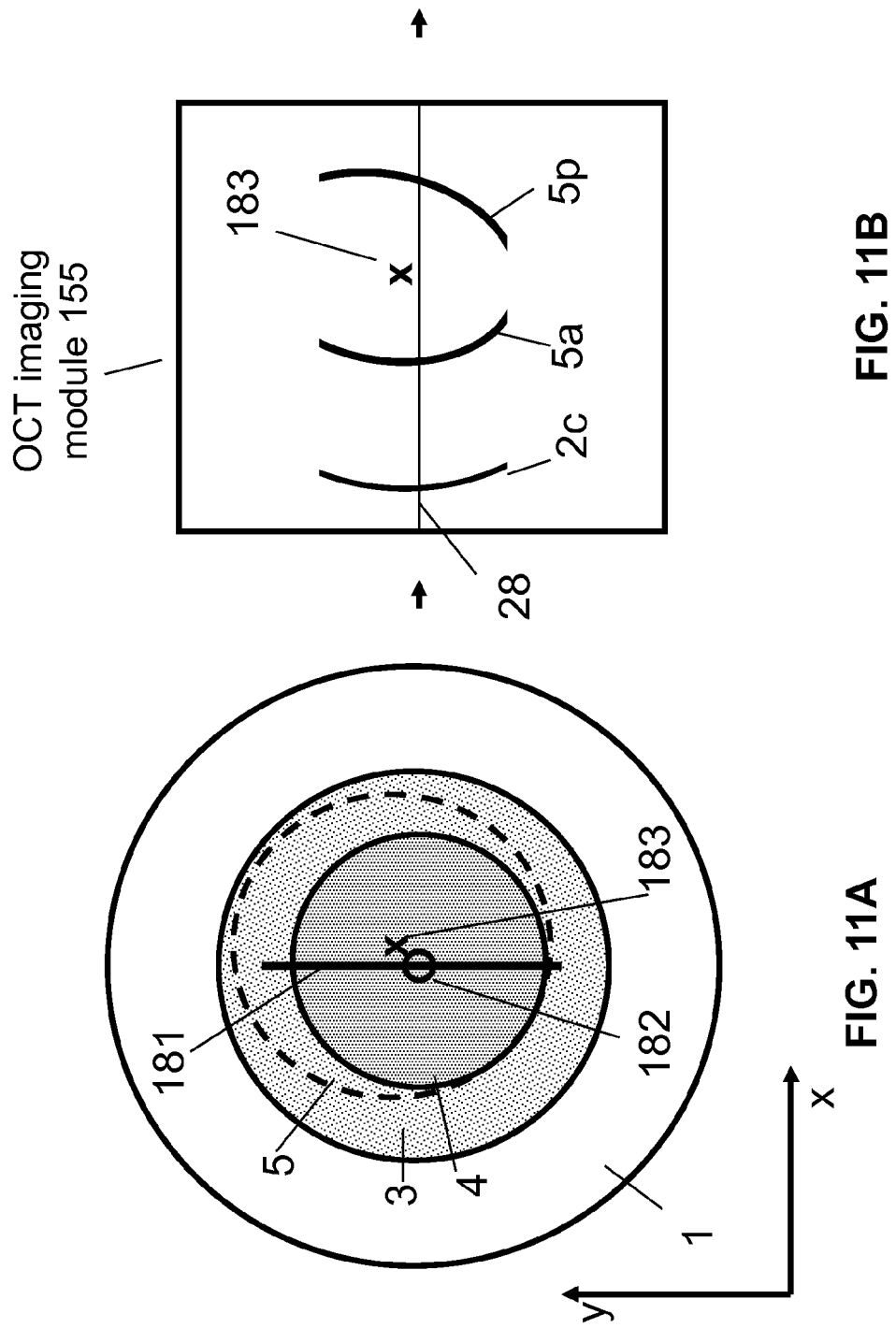

FIG. 11A illustrates that the OCT imaging system 150 can perform fast one dimensional (1D) scans, such as a line scan 181. When the lens 5, shown by a dotted line as it may not be directly visible by a video microscope, is not concentric with the pupil 4, typically a center 182 of the OCT scan does not coincide with a center 183 of the lens 5.

FIG. 11B illustrates that in this off-center case the OCT image of the lens 5 on an OCT imaging module 155 displaying the 1D scan along the line 181 can exhibit a partial image 2*c* of the cornea, an image 5*a* of the anterior capsular surface and an image 5*p* of the posterior capsular surface. The tilted and off-center position of the capsular surfaces 5*a* and 5*p* can be indicative of the center 183 of the lens 5 being off the optical axis 28 of the imaging system 100 and the optical axis 8 of the lens 5 being tilted relative to the optical axis 28. Other OCT implementations can generate and display two-dimensional (2D) images by raster-scanning the lens 5.

FIGS. 11C-D illustrate that the surgeon can determine the misalignment of a reference element of the imaging system 110 and the imaged lens 5 from the analysis of the OCT image shown by the OCT imaging module 155 and then proceed analogously to the method 200. In particular, the surgeon can enter a fixation light control command through the input module 135 of the fixation light controller 130 in accordance with the determined misalignment. This command can generate an electronic control signal for the fixation light source 140 to adjust the fixation light 145 such that the adjusted light guides the patient to move his/her eyes to reduce the misalignment.

While this specification contains many specifics, these should not be construed as limitations on the scope of the invention or of what can be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features can be described above as acting in certain combinations and even initially claimed as such, one or more features from a claimed combination can in some cases be excised from the combination, and the claimed combination can be directed to a subcombination or variation of a subcombination.

The invention claimed is:

1. An ophthalmic system, comprising:
an eye-docking system, including a docking tip with a partially transparent patient interface, dockable to an eye with vacuum suction;
an ophthalmic imaging device comprising a first imaging system configured to generate a first image of an anterior portion of an imaged eye of a patient through the patient interface and an OCT imaging system configured to generate an OCT image of the anterior portion of the imaged eye of the patient through the patient interface;
wherein the ophthalmic imaging device is configured to:
  computer-generate and display a reference feature on the first image of the anterior portion of the imaged eye, related to the docking tip of the ophthalmic system;
analyze the OCT image;
  based on the analysis of the OCT image, determine a misalignment of a lens of the imaged eye and the reference feature; and
  display to a user a directional indicator indicating how a fixation light should be moved to reduce the misalignment of the lens of the imaged eye and the reference feature wherein the directional indicator is displayed as a visual overlay on the first image;
a fixation light controller, comprising
  an input module, configured to receive an input from the user in relation to the directional indicator, and
  a control signal generator that generates a fixation light control signal in response to the received input; and
a patient-fixation light source, configured
  to receive the fixation light control signal, and
  to generate an adjusted fixation light according to the received fixation light control signal;
wherein the reference feature displayed on the first image comprises a targeting circle that corresponds to an outline of the docking tip.

2. The ophthalmic system of claim 1, wherein:
the first imaging system of the ophthalmic imaging device comprises at least one of a microscope, an ophthalmic microscope, a stereo microscope.

3. The ophthalmic system of claim 1, wherein:
the first imaging system of the ophthalmic imaging device-comprises:
  an electronic sensing system that senses a collected imaging light from the imaged eye, including at least one of
    a Charge-Coupled Device (CCD) array, a Complementary Metal-Oxide Semiconductor (CMOS) array, a pixel-array, and an electronic sensor array; and
  an electronic display system that displays the image of a portion of the imaged eye in relation to the sensed collected imaging light, including at least one of
    a Light Emitting Diode (LED) display, a plasma screen, an electronic display, a computer display, a Liquid Crystal Display (LCD) screen, a Cathode Ray Tube (CRT) display, a video-module, a video microscope display, a stereo video microscope display, a high definition (HD) video microscope, a processor-based image system, and an opto-mechanical projector.

4. The ophthalmic system of claim 1, the ophthalmic imaging device comprising:
an image-processor, configured
to analyze the OCT image of the portion of the imaged eye and the reference feature; and
to determine a measure of the misalignment of the imaged eye and the docking tip of the imaging device; and
the OCT imaging module is configured to display an indication of the measure of the misalignment, determined by the image-processor.

5. The ophthalmic system of claim 1, wherein:
the input module is configured to receive an electronic, mechanical, optical, or sensed input.

6. The ophthalmic system of claim 1, the input module comprising:
a touch-pad, a touch-screen, a joystick, an electro-mechanical sensor, a position sensor, an optical sensor, a voice-prompted actuator, or an electro-mechanical controller.

7. The ophthalmic system of claim 1, the patient-fixation light source comprising at least one of:
a LED array, a plasma screen, an electronic display, a computer display, an LCD screen, a video-module, an opto-mechanical projector, a CRT display, a slit-lamp, a processor-based image system, and a light-source movable by an electro-mechanical actuator.

8. The ophthalmic system of claim 1, wherein:
the patient-fixation light source is configured
to display the fixation light for a non-imaged eye of the patient; and
to move the displayed fixation light according to the received fixation light control signal to assist a reduction of a misalignment between the imaged eye and the docking tip of the ophthalmic system.

9. The ophthalmic system of claim 1, wherein:
the patient-fixation light source is configured
to generate the fixation light for the imaged eye of the patient; and
to adjust the generated fixation light according to the received fixation light control signal to assist a reduction of a misalignment between the imaged eye and docking tip of the ophthalmic system.

10. The ophthalmic system of claim 1, wherein the reference feature displayed on the first image indicates an optical axis of the ophthalmic imaging device centered within the docking tip.

11. A method of aligning an eye with an ophthalmic system, the method comprising:
preparing an eye-docking system, including a docking tip with a partially transparent patient interface, dockable to an eye with vacuum suction;
preparing an ophthalmic imaging device comprising a first imaging system, an OCT imaging system, and an electronically adjustable patient-fixation light system;
generating, by the first imaging system, a first image of an anterior portion of an imaged eye of a patient through the partially transparent patient interface;
generating, by the OCT imaging system, an OCT image of the anterior portion of the imaged eye of the patient through the partially transparent patient interface;
determining, by the ophthalmic imaging device, a misalignment of a lens of the imaged eye relative to a reference feature of the imaging device based on an analysis of the OCT image displayed by the OCT imaging system, wherein the reference feature comprises a targeting circle that corresponds to an outline of the docking tip;
displaying a directional indicator indicating how a fixation light should be moved to reduce the misalignment of the lens of the imaged eye relative to the reference feature of the imaging device, wherein the directional indicator is displayed as a visual overlay on the first image;
adjusting a fixation light of the patient-fixation light system by generating an electronic control signal according to the determined misalignment to cause the alignment of the imaged eye relative to the imaging device; and
docking the docking tip to the aligned eye.

12. The method of claim 11, wherein the first imaging system comprises:
a microscope, an ophthalmic microscope, a stereo microscope, a video microscope, a Light Emitting Diode (LED) display, a plasma screen, an electronic display, a computer display, a Liquid Crystal Display (LCD) screen, a Cathode Ray Tube (CRT) display, a video-module, a video microscope display, a stereo video microscope display, a high definition (HD) video microscope, a processor-based image system, or an opto-mechanical projector.

13. The method of claim 11, wherein the determining the misalignment comprises:
determining at least one of a lateral misalignment and a rotational misalignment.

14. The method of claim 11, wherein the determining the misalignment comprises:
determining the misalignment with an active assistance of the imaging device, the imaging device displaying an image of a portion of the imaged eye, a reference feature and a misalignment indicator.

15. The method of claim 11, wherein the adjusting of the fixation light comprises:
generating the electronic control signal with a fixation light controller, wherein
the fixation light controller comprises at least one of a touch-pad, a touch-screen, a joystick, an electro-mechanical sensor, a position sensor, an optical sensor, a voice-prompted actuator, and an electro-mechanical controller.

16. The method of claim 11, wherein the generating the electronic control signal comprises:
generating the electronic control signal to cause a patient-fixation light source to generate the fixation light to guide the patient to reduce the determined misalignment.

17. The method of claim 16, the patient-fixation light source comprising at least one of:
a LED array, a plasma screen, an electronic display, a computer display, an LCD display, a CRT display, a video-module, a slit-lamp, a processor-based image system, and a light-source movable by an electro-mechanical actuator.

18. The method of claim 16, wherein the generating the electronic control signal comprises:
generating the electronic control signal for at least one of the imaged eye and a non-imaged eye.

19. The method of claim 11, wherein:
the determining the misalignment and the controlling the fixation light are repeated iteratively.

20. The method of claim 11, wherein the reference feature indicates an optical axis of the ophthalmic imaging device centered within the docking tip.

* * * * *